US010183062B2

(12) United States Patent
Minton et al.

(10) Patent No.: US 10,183,062 B2
(45) Date of Patent: Jan. 22, 2019

(54) TREATMENT FOR CANCER

(71) Applicant: The University of Nottingham, Nottingham Nottinghamshire (GB)

(72) Inventors: Nigel Peter Minton, Nottingham (GB); John Timothy Heap, Nottingham (GB)

(73) Assignee: THE UNIVERSITY OF NOTTINGHAM, Nottinghamshire (GB)

( * ) Notice: Subject to any disclaimer, the term of this patent is extended or adjusted under 35 U.S.C. 154(b) by 0 days.

(21) Appl. No.: 15/038,345

(22) PCT Filed: Nov. 24, 2014

(86) PCT No.: PCT/GB2014/053461
§ 371 (c)(1),
(2) Date: May 20, 2016

(87) PCT Pub. No.: WO2015/075475
PCT Pub. Date: May 28, 2015

(65) Prior Publication Data
US 2016/0287675 A1   Oct. 6, 2016

(30) Foreign Application Priority Data

Nov. 22, 2013   (GB) .................................. 1320679.2

(51) Int. Cl.
| | |
|---|---|
| *A61K 38/44* | (2006.01) |
| *A61K 31/396* | (2006.01) |
| *A61K 35/742* | (2015.01) |
| *A61K 9/00* | (2006.01) |
| *C12N 15/74* | (2006.01) |
| *C12N 9/06* | (2006.01) |
| *A61K 35/745* | (2015.01) |

(52) U.S. Cl.
CPC ............ *A61K 38/44* (2013.01); *A61K 9/0019* (2013.01); *A61K 31/396* (2013.01); *A61K 35/742* (2013.01); *A61K 35/745* (2013.01); *C12N 9/0028* (2013.01); *C12N 15/74* (2013.01); *C12Y 105/01034* (2013.01)

(58) Field of Classification Search
None
See application file for complete search history.

(56) References Cited

U.S. PATENT DOCUMENTS

| | | | |
|---|---|---|---|
| 6,416,754 B1* | 7/2002 | Brown ............... | A61K 48/0058 424/93.21 |
| 6,652,849 B2* | 11/2003 | Brown ............... | A61K 48/0058 424/93.2 |
| 6,984,513 B2* | 1/2006 | Brown ............... | A61K 35/742 424/93.41 |
| 2007/0059329 A1 | 3/2007 | Norais et al. | |

FOREIGN PATENT DOCUMENTS

| | | |
|---|---|---|
| WO | WO 2000/047725 A1 | 8/2000 |
| WO | WO 2006/103452 A2 | 10/2006 |
| WO | WO 2015/075475 A1 | 5/2015 |

OTHER PUBLICATIONS

Hu, et al. (2003) "Nitroaryl Phosphoramides as Novel Prodrugs for *E. coli* Nitroreductase Activation in Enzyme Prodrug Therapy", Journal of Medicinal Chemistry, 46: 4818-21.*
Zhou, et al. (2016) "Intravenous Administration Is an Effective and Safe Route for Cancer Gene Therapy Using the Bifidobacterium-Mediated Recombinant HSV-1 Thymidine Kinase and Ganciclovir", International Journal of Molecular Sciences, 17(6): online: pp. 1-18.*
Liu, et al. (2008) "Optimized Clostridia-Directed Enzyme Prodrug Therapy Improves the Antitumor Activity of the Novel DNA-Cross-Linking Agent PR-104", Cancer Research, 68(19): 7995-8003.*
Voak, et al. (2013) "An Essential Type I Nitroreductase from Leishmania major Can Be Used to Activate Leishmanicidal Prodrugs", The Journal of Biological Chemistry, 288(40): 28466-76.*
Voak, et al. (Oct. 28, 2013 online) "Evaluating aziridinyl nitrobenzamide compounds as leishmanicidal prodrugs" Antimicrobial Agents and Chemotherapy, 28 pages long.*
Jean, et al. (2008) "Bacterial Therapies: Completing the Cancer Treatment Toolbox", Current Opinion in Biotechnology, 19(5): 511-17.*
Heap, et al. (2012) "Integration of DNA into bacterial chromosomes from plasmids without a counter-selection marker", Nucleic Acids Research, 40(8): e59 (20 pages long).*
Dykhuizen (2005) :Species Numbers in Bacteria—Procedings of the California Academy of Sciences, 56(6 Suppl 1): 62-71.*
Knox, et al. (1988) "A new cytotoxic, DNA interstrand crosslinking agent, 5-(aziridin-1-yl)-4-hydroxylamino-2-nitrobenzamide, is formed from 5-(aziridin-1-yl)-4-hydroxylamino-2-nitrobenzamide, is formed from ... (CB 1954) by a nitroreductase enzyme in walker carcinoma cells", Biochem. Pharm., 37(24):4661-69.*
Anlezark et al., "Bacillus amyloliquefaciens orthologue of Bacillus subtilis ywrO encodes a nitroreductase enzyme which activates the prodrug CB 1954." Microbiology (2002); 148.1: 297-306.

(Continued)

*Primary Examiner* — Robert M Kelly
(74) *Attorney, Agent, or Firm* — Cooley LLP

(57) ABSTRACT

The present invention provides a method of treatment for cancer in a subject comprising the administration of a prodrug, wherein the subject is colonised with an obligate anaerobic microorganism capable of expressing a polypeptide having nitroreductase activity, wherein the polypeptide exhibits preferential reduction of CB1954 to a 4-hydroxylamine (4HX) derivative instead of a 2-hydroxylamine derivative; and is capable of reducing CB1954 to the 4HX derivative with a $K_m$ of less than 30 micromolar. The present invention further provides an isolated polypeptide, nucleic acids encoding said polypeptide, vectors and host cells comprising said nucleic acids and vectors and uses of the above in treating solid tumours.

Figure 1:
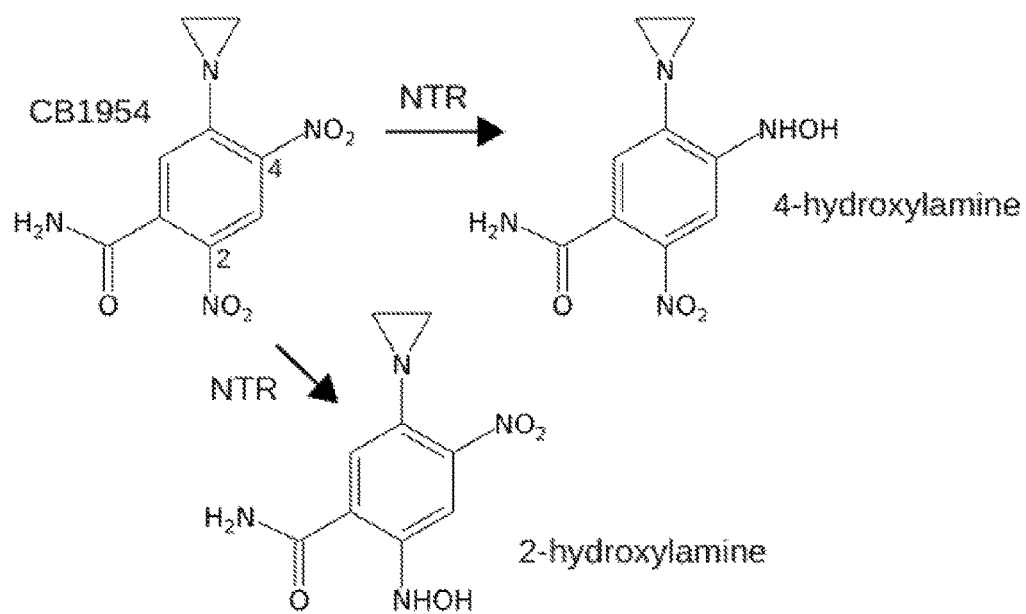

18 Claims, 3 Drawing Sheets
Specification includes a Sequence Listing.

(56) References Cited

OTHER PUBLICATIONS

Anlezark et al., "The bioactivation of 5-(aziridin-1-yl)-2, 4-dinitrobenzamide (CB1954)-I: purification and properties of a nitroreductase enzyme from *Escherichia coli*—a potential enzyme for antibody-directed enzyme prodrug therapy (ADEPT)." Biochemical Pharmacology (1992); 44.12: 2289-2295.
Berg et al., "Summary statement of the Asilomar conference on recombinant DNA molecules." Proceedings of the National Academy of Sciences (1975); 72.6: 1981-1984.
Bettegowda et al., "The genome and transcriptomes of the antitumor agent Clostridium novyi-NT." Nature Biotechnology (2006); 24.12: 1573-1580.
Breitbach et al., "Intravenous delivery of a multi-mechanistic cancer-targeted oncolytic poxvirus in humans." Nature (2011); 477.7362: 99-102.
Carey et al., "Clostridial oncolysis in man." European Journal of Cancer (1967); 3.1: 37-46.
Chung-Faye et al., "Virus-directed, Enzyme Prodrug Therapy with Nitroimidazole Reductase A Phase I and Pharmacokinetic Study of its Prodrug, CB1954." Clinical Cancer Research (2001); 7.9: 2662-2668.
Dang et al., "Combination bacteriolytic therapy for the treatment of experimental tumors." Proceedings of the National Academy of Sciences (2001); 98.26: 15155-15160.
Danino et al., "In vivo gene expression dynamics of tumor-targeted bacteria." ACS Synthetic Biology (2012); 1.10: 465-470.
Diaz, Jr. et al., "Pharmacologic and toxicologic evaluation of C. novyi-NT spores." Toxicological Sciences (2005); 88.2: 562-575.
Emptage et al., "Nitroreductase from Bacillus licheniformis: a stable enzyme for prodrug activation." Biochemical Pharmacology (2009); 77.1: 21-29.
Forbes, N.S., "Engineering the perfect (bacterial) cancer therapy." Nature Reviews Cancer (2010); 10.11: 785-794.
Fox et al., "Genetically modified Clostridium for gene therapy of tumors." Gene Therapy of Cancer: Methods and Protocols (2000); 25: 413-418.
Grove et al., "Generation of *Escherichia coli* nitroreductase mutants conferring improved cell sensitization to the prodrug CB1954." Cancer Research (2003); 63.17: 5532-5537.
Hacein-Bey-Abina et al., "Insertional oncogenesis in 4 patients after retrovirus-mediated gene therapy of SCID-X1." J Clin Invest. (2008); 118(9): 3132-3142. doi:10.1172/JCI35700.
Heap, J.T. et al., "A modular system for Clostridium shuttle plasmids." Journal of Microbiological Methods (2009); 78.1: 79-85.
Heap, J.T. et al., "Integration of DNA into bacterial chromosomes from plasmids without a counter-selection marker." Nucleic Acids Research (2012); 40.8: e59-e59.
Heap, J.T. et al., "The ClosTron: a universal gene knock-out system for the genus Clostridium." Journal of Microbiological Methods (2007); 70.3: 452-464.
Heap, J.T. et al., "The ClosTron: Mutagenesis in Clostridium refined and streamlined." Journal of Microbiological Methods (2010); 80.1: 49-55.
Heap, John T., et al. "Spores of Clostridium engineered for clinical efficacy and safety cause regression and cure of tumors in vivo." Oncotarget (2014); 5: 1761-1769.
Helsby et al., "2-Amino metabolites are key mediators of CB 1954 and SN 23862 bystander effects in nitroreductase GDEPT." British Journal of Cancer (2004); 90.5: 1084-1092.
Jaberipour et al., "Testing double mutants of the enzyme nitroreductase for enhanced cell sensitisation to prodrugs: effects of combining beneficial single mutations." Biochemical Pharmacology (2010); 79.2: 102-111.
Jarrom et al., "Steady-state and stopped-flow kinetic studies of three *Escherichia coli* NfsB mutants with enhanced activity for the prodrug CB1954." Biochemistry (2009); 48.32: 7665-7672.
Knox et al., "A new cytotoxic, DNA interstrand crosslinking agent, 5-(aziridin-1-yl)-4-hydroxylamino-2-nitrobenzamide, is formed from 5-(aziridin-1-yl)-2, 4-dinitrobenzamide (CB 1954) by a nitroreductase enzyme in Walker carcinoma cells." Biochemical Pharmacology (1988); 37.24: 4661-4669.
Knox et al., "Bioactivation of 5-(aziridin-1-yl)-2, 4-dinitrobenzamide (CB 1954) by human NAD (P) H quinone oxidoreductase 2: a novel co-substrate-mediated antitumor prodrug therapy." Cancer Research (2000); 60.15: 4179-4186.
Lambin et al., "Colonisation of Clostridiumin the body is restricted to hypoxic and necrotic areas of tumours." Anaerobe (1998); 4.4: 183-188.
Lambowitz and Zimmerly, "Mobile group II introns." Annu. Rev. Genet. (2004); 38: 1-35.
Lemmon, M. J., et al. "Anaerobic bacteria as a gene delivery system that is controlled by the tumor microenvironment." Gene Therapy (1997); 4(8): 791-796.
Liu et al., "Anticancer efficacy of systemically delivered anaerobic bacteria as gene therapy vectors targeting tumor hypoxia/necrosis." Gene Therapy (2002); 9.4: 291-296.
Liu, Shie-Chau, et al. "Optimized Clostridium-directed enzyme prodrug therapy improves the antitumor activity of the novel DNA cross-linking agent PR-104." Cancer Research (2008); 68(19): 7995-8003.
Malmgren and Flanigan, "Localization of the vegetative form of Clostridium tetani in mouse tumors following intravenous spore administration." Cancer Research (1955), 15.7: 473-478.
McNeish, I. A., et al. "Virus directed enzyme prodrug therapy for ovarian and pancreatic cancer using retrovirally delivered *E. coli* nitroreductase and CB 1954." Gene Therapy (1998); 5(8): 1061-1069.
Michael et al., "Physical characterisation of the *Escherichia coli* B gene encoding nitroreductase and its over-expression in *Escherichia coli* K12." FEMS Microbiology Letters (1994); 124.2: 195-202.
Minton, "Clostridia in cancer therapy." eds Bahl H, Durre P (Wiley-VCH Verlag GmbH). Nature Reviews Microbiology (2003); 1.3: 1-7.
Möse and Möse, "Oncolysis by Clostridia. I. Activity of Clostridium Butyricum (M-55) and Other Nonpathogenic Clostridia against the Ehrlich Carcinoma." Cancer Research (1964), 24.2 Part 1 (1964): 212-216.
Palmer et al., "Mechanism of cell death induced by the novel enzyme-prodrug combination, nitroreductase/CB1954, and identification of synergism with 5-fluorouracil." British Journal of Cancer (2003); 89.5: 944-950.
Parker et al., "Effect of histolyticus infection and toxin on transplantable mouse tumors." Experimental Biology and Medicine (1947); 66.2: 461-467.
PCT/GB2014/053461, International Preliminary Report on Patentability dated May 24, 2016, 8 pages.
PCT/GB2014/053461, International Search Report and Written Opinion dated Feb. 20, 2015, 13 pages.
Pipiya et al., "Hypoxia reduces adenoviral replication in cancer cells by downregulation of viral protein expression." Gene Therapy (2005); 12.11: 911-917.
Prosser et al., "Discovery and evaluation of *Escherichia coli* nitroreductases that activate the anti-cancer prodrug CB1954." Biochemical Pharmacology (2010); 79.5: 678-687.
Race et al., "Kinetic and structural characterisation of *Escherichia coli* nitroreductase mutants showing improved efficacy for the prodrug substrate CB1954." Journal of Molecular Biology (2007); 368.2: 481-492.
Savers, Screen, Savers, Screen. "Assessment of adenoviral vector safety and toxicity: report of the National Institutes of Health Recombinant DNA Advisory Committee." Human Gene Therapy (2002); 13.1: 3-13.
Shen and Hermiston, "Effect of hypoxia on Ad5 infection, transgene expression and replication." Gene Therapy (2005); 12.11: 902-910.
Smith et al., "Discodermolide analogues as the chemical component of combination bacteriolytic therapy." Bioorganic & Medicinal Chemistry Letters (2005); 15.15: 3623-3626.
Swe et al., "Targeted mutagenesis of the Vibrio fischeri flavin reductase FRase I to improve activation of the anticancer prodrug CB1954." Biochemical Pharmacology (2012); 84.6: 775-783.

(56) References Cited

OTHER PUBLICATIONS

Theys et al., "Repeated cycles of Clostridium-directed enzyme prodrug therapy result in sustained antitumour effects in vivo." British Journal of Cancer (2006); 95.9: 1212-1219.

Vass et al., "*E. coli* NfsA: an alternative nitroreductase for prodrug activation gene therapy in combination with CB1954." British Journal of Cancer (2009); 100.12: 1903-1911.

Zhao et al., "Monotherapy with a tumor-targeting mutant of *Salmonella typhimurium* cures orthotopic metastatic mouse models of human prostate cancer." Proceedings of the National Academy of Sciences (2007); 104.24: 10170-10174.

Zhao et al., "Tumor-targeting bacterial therapy with amino acid auxotrophs of GFP-expressing *Salmonella typhimurium*." Proceedings of the National Academy of Sciences of the United States of America (2005); 102.3: 755-760.

\* cited by examiner

SEQUENCE LISTING

<160> NUMBER OF SEQ ID NOS: 4

<210> SEQ ID NO 1
<211> LENGTH: 221
<212> TYPE: PRT
<213> ORGANISM: Neisseria meningitidis

<400> SEQUENCE: 1

```
Met Thr Val Leu Ser Lys Glu Gln Val Leu Ser Ala Phe Lys Asn Arg
1               5                   10                  15

Lys Ser Cys Arg His Tyr Asp Ala Ala Arg Lys Ile Ser Ala Glu Asp
            20                  25                  30

Phe Gln Phe Ile Leu Glu Leu Gly Arg Leu Ser Pro Ser Ser Val Gly
        35                  40                  45

Ser Glu Pro Trp Gln Phe Ile Val Val Gln Asn Pro Glu Ile Arg Gln
    50                  55                  60

Ala Ile Lys Pro Phe Ser Trp Gly Met Ala Asp Ala Leu Asp Thr Ala
65                  70                  75                  80

Ser His Leu Val Val Phe Leu Ala Lys Lys Asn Ala Arg Ser Asp Ser
                85                  90                  95
```

```
Pro Phe Met Leu Glu Ser Leu Lys Arg Arg Gly Val Thr Glu Pro Asp
                100                 105                 110

Ala Val Ala Lys Ser Leu Ala Arg Tyr Gln Ala Phe Gln Ala Asp Asp
            115                 120                 125

Ile Lys Ile Leu Asp Asp Ser Arg Ala Leu Phe Asp Trp Cys Cys Arg
130                 135                 140

Gln Thr Tyr Ile Ala Leu Ala Asn Met Met Thr Gly Ala Ala Met Ala
145                 150                 155                 160

Gly Ile Asp Ser Cys Pro Val Glu Gly Phe Asn Tyr Ala Glu Met Glu
                165                 170                 175

Arg Ile Leu Ser Gly Gln Phe Gly Leu Phe Asp Ala Ala Glu Trp Gly
            180                 185                 190

Val Ser Val Ala Ala Thr Phe Gly Tyr Arg Val Gln Glu Ile Ala Thr
        195                 200                 205

Lys Ala Arg Arg Pro Leu Glu Glu Thr Val Ile Trp Ala
    210                 215                 220

<210> SEQ ID NO 2
<211> LENGTH: 220
<212> TYPE: PRT
<213> ORGANISM: Haemophilus somnus

<400> SEQUENCE: 2

Met Thr Thr Ile Ser Lys Glu His Val Leu Asp Ser Phe Asn Arg Arg
1               5                   10                  15

Ala Ser Thr Arg Tyr Tyr Asp Pro Asn Lys Lys Ile Ser Asn Glu Asp
            20                  25                  30

Phe Ser Tyr Val Leu Glu Phe Ala Arg Leu Ser Pro Ser Ser Val Gly
        35                  40                  45

Ser Glu Pro Trp His Phe Leu Val Ile Gln Asn Pro Glu Leu Arg Ala
    50                  55                  60

Lys Leu Lys Pro Val Ser Trp Gly Met Ala Thr Gln Ile Asp Asp Ala
65                  70                  75                  80

Ser His Leu Val Val Ile Leu Ala Lys Lys Asn Ala Arg Tyr Asp Ser
                85                  90                  95

Glu Phe Leu Val Gln Ser Met Lys Arg Gly Leu Ser Gly Glu Gln
                100                 105                 110

Ile Gln Ala Thr Lys Glu Lys Tyr His Leu Phe Gln Ala Glu His Met
            115                 120                 125

Lys Thr Leu Glu Asn Asp Arg Thr Leu Phe Asp Trp Ala Ser Lys Gln
130                 135                 140

Thr Tyr Ile Ala Leu Ala Asn Met Leu Thr Gly Ala Ala Leu Ile Gly
145                 150                 155                 160

Ile Asp Ser Cys Pro Ile Glu Gly Phe Asn Tyr Glu Lys Val Asn Gln
                165                 170                 175

Ile Leu Thr Asp Ala Gly Val Leu Asp Ser Asp Glu Trp Gly Val Ser
            180                 185                 190

Val Met Ala Thr Phe Gly Tyr Arg Ala Lys Glu Ile Lys Pro Lys Ser
        195                 200                 205

Arg Lys Ser Leu Asp Glu Ile Val Thr Trp Val Lys
    210                 215                 220

<210> SEQ ID NO 3
<211> LENGTH: 666
<212> TYPE: DNA
<213> ORGANISM: Neisseria meningitidis
```

```
<400> SEQUENCE: 3
atgacagtat taagcaaaga gcaggttcta tccgcattta aaaaccgtaa atcatgccgg    60
cattacgatg cggcacgcaa aatcagtgcc gaggattttc agtttatttt agaactcggg   120
cgtttgtcgc ccagttcggt cggttcggag ccttggcagt ttattgtggt tcaaaaccct   180
gaaatccgac aggcaatcaa gccgtttttct tggggtatgg cggatgcttt ggataccgcc   240
agtcatttgg tggtgttttt ggcgaagaaa aatgcccgct ccgacagccc gtttatgttg   300
gaaagcctca acggcgcgg cgttaccgaa ccggatgccg tagcaaaatc tttggcaagg   360
tatcaggcgt ttcaagctga cgacatcaag attttggacg attctcgcgc cttgtttgac   420
tggtgttgcc gtcagaccta tatcgcgtta gccaacatga tgacgggtgc ggcgatggca   480
ggtatcgatt cctgcccggt ggaaggtttc aactatgccg agatggagcg catattgtcc   540
gggcagtttg gtttgttcga tgcggcagaa tggggcgtgt ccgtcgccgc gacattcggc   600
taccgcgttc aggaaatcgc cacgaaagcg cgtaggccct tggaagaaac cgttatttgg   660
gcataa                                                               666

<210> SEQ ID NO 4
<211> LENGTH: 662
<212> TYPE: DNA
<213> ORGANISM: Haemophilus somnus

<400> SEQUENCE: 4
atgacgacta tttcaaaaga acacgtgctg gatagtttta atcgtcgtgc atccacacgt    60
tactatgatc caaataaaaa aatcagcaat gaagatttct cttatgtttt ggaatttgct   120
cgcctttcgc caagttctgt cggctctgaa ccttggcatt ttttagtaat ccaaaatccg   180
gaactacggg caaaattaaa acctgtcagc tggggaatgg caactcaaat tgacgatgcc   240
agtcatttag ttgttatctt agcgaaaaag aatgcacgct atgattcaga attttttagta   300 caatccatga aaagacgtgg gttatccggc gaacaaatac aagctaccaa agaaaaatat   360
catctctttc aagcagaaca tatgaaaacg cttgagaatg accgcacttt atttgactgg   420
gcaagtaaac aaacctatat tgccttagca aatatgttaa ctggtgctgc attaattgga   480
atagacagtt gtccaattga aggtttaat tatgaaaaag taaatcaaat tttaactgac   540
gcaggtgtat tagattcaga gaatgggggag ttcggtaat ggcaactttc ggctaccgag   600
caaaagaaat taagccaaaa tcccgtaaat cccttgatga aatcgtcact tgggttaaat   660
aa                                                                  662
```

TREATMENT FOR CANCER

CROSS-REFERENCE TO RELATED APPLICATIONS

This application is a U.S. National Stage Entry of PCT/GB2014/053461 filed Nov. 24, 2014, the contents of which are herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BABR-002_01US_SeqList_St25.txt, date recorded May 5, 2016, file size 6kb)

BACKGROUND

Biotechnology potentially offers unconventional routes to new cancer therapies, and research in this area has focused on using viruses as vectors to deliver therapeutic genes to tumours. Unfortunately, serious issues with the safety of viral vectors have been encountered (1, 2) and only recently has a virus system showing good specificity and tumour infiltration been described (3). Several types of bacteria have also been investigated as delivery vectors, and as therapeutics in their own right (4). Spores of some species of *Clostridium*, which are strictly anaerobic bacteria, naturally target tumours with high specificity following intravenous administration, because the dormant spores can germinate and grow only in the hypoxic cores of solid tumours (5-7) which are difficult to target using viral vectors (8, 9). The growing bacteria secrete proteases inside the tumour, rapidly digesting the tumour mass. This approach is especially interesting because it directly targets the hypoxic cells in poorly vascular regions which tend to be refractory to conventional treatments. Any *Clostridium* cells entering normal tissue from a colonized tumour would be poisoned by oxygen and die. Stringent spacial containment by oxygen is an excellent safety feature absent from treatments using aerobic bacteria (10, 11).

Augmentation of the anti-tumour effect of *Clostridium* strains has been sought by genetically modifying them to express therapeutic proteins, mainly enzymes which sensitize the tumour to certain chemotherapeutic agents (13-17). The 'prodrug' CB1954 (5-(aziridin-1-yl)-2,4-dinitrobenzamide) shown in FIG. 1 is an attractive candidate because its clinical safety has been demonstrated (18) and a 10,000-fold increase in toxicity is achieved upon its activation by a suitable nitroreductase (NTR) enzyme to the 4-hydroxylamine (4HX) derivative (5-(aziridin-1-yl)-4-hydroxylamino-2-nitrobenzamide) which is a DNA cross-linking agent (19).

SUMMARY OF THE INVENTION

For *Clostridium*-Directed Enzyme-Prodrug Therapy (CDEPT) using CB1954 to be suitable for clinical evaluation, two issues must be addressed. Firstly, the poor kinetics of CB1954 activation by known NTRs must be improved upon. The maximum concentration of CB1954 which can be safely achieved in patient serum is only 6.3 µM (18), at which concentration previously-reported enzymes are not saturated. Secondly, a recombinant *Clostridium* strain must be constructed with properties appropriate for clinical application. The DNA encoding the prodrug-converting enzyme may be stably localized to the chromosome rather than carried by a plasmid, antibiotic-resistance gene(s) used during strain construction must be removed, and the organism may be disabled to prevent its growth in the event of a release into the environment. A strain meeting these criteria has not been described in any report to-date.

The present inventors have surprisingly solved each of these problems and demonstrated the efficacy of CDEPT in a mouse xenograft model of human colon carcinoma, using CB1954 and a recombinant *Clostridium* strain. Novel NTRs which demonstrate improved kinetics of CB1954 activation compared to known NTRs were identified and stably localized to the chromosome of a recombinant *Clostridium* strain that is auxotrophic for uracil (thus preventing its growth in the absence of uracil supplementation).

According to a first aspect of the present invention, there is provided a method of treatment for cancer in a subject comprising the administration to the subject of spores of an obligate anaerobic microorganism capable of expressing a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar.

According to another aspect of the present invention, there is provided a method of preparing a subject for treatment with a prodrug for cancer comprising the administration to the subject of spores of an obligate anaerobic microorganism capable of expressing a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar.

According to another aspect of the present invention, there is provided a method of treatment for cancer in a subject comprising the administration of a prodrug, wherein the subject is colonised with an obligate anaerobic microorganism capable of expressing a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar.

According to a yet further aspect, the invention provides an obligate anaerobic microorganism capable of expressing a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar,
for use as a medicament, preferably for the treatment of cancer.

According to a further aspect, the invention provides an obligate anaerobic microorganism capable of expressing a polypeptide having nitroreductase activity, wherein the polypeptide:
  exhibits preferential reduction of CB1954 to a 4-hydroxylamine (4HX) derivative instead of a 2-hydroxylamine derivative; and is capable of reducing CB1954 to the 4HX derivative with a $K_m$ of less than 30 micromolar,
for use in the preparation of a medicament for the treatment of cancer.

According to a further aspect, the invention provides the use of an obligate anaerobic microorganism to convert a prodrug to a drug active in situ in a tumour, such as a solid tumour, wherein the obligate anaerobic microorganism is capable of expressing a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar, According to another aspect of the invention, there is provided an isolated polypeptide having nitroreductase activity wherein the isolated polypeptide:
  a. exhibits preferential reduction of CB1954 to a 4-hydroxylamine (4HX) derivative instead of a 2-hydroxylamine derivative (2HX); and
  b. is capable of reducing CB1954 to the 4HX derivative with a $K_m$ of less than 30 micromolar.

Another aspect of the invention provides an isolated polynucleotide encoding the polypeptide according to the invention.

Another aspect of the invention provides a vector comprising the polynucleotide according to the invention.

Another aspect of the invention provides an obligate anaerobic microorganism expressing or capable of expressing a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar.

Another aspect of the invention provides a host cell capable of expressing the polypeptide defined in the invention.

Another aspect of the invention provides a pharmaceutical composition comprising an polypeptide according to the invention, a polynucleotide according to the invention, a vector according to the invention or a host cell according to the invention together with pharmaceutically acceptable carrier, vehicle, diluent and/or excipient.

Another aspect of the invention provides the composition according to the invention is for use in medicine.

Another aspect of the invention provides the composition according to the invention for use in directed enzyme prodrug therapy (DEPT), such as Clostridial directed enzyme prodrug therapy (CDEPT).

Another aspect of the present invention provides a method of treating solid tumours comprising or consisting of administering an effective amount of the polypeptide, polynucleotide, vector, host cell or pharmaceutical composition described above.

Another aspect of the present invention provides a prodrug for use as a medicament in a subject colonised with an obligate anaerobic microorganism capable of expressing a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar.

Another aspect of the present invention provides a prodrug for use in the preparation of a medicament for use in a subject colonised with an obligate anaerobic microorganism capable of expressing a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar.

DETAILED DESCRIPTION

The subject may be colonised with the obligate anaerobic microorganism by administration of the obligate anaerobic microorganism. A tumour of the subject may be colonised with the obligate anaerobic microorganism by administration of the obligate anaerobic microorganism. In embodiments or aspects of the invention where the obligate anaerobic microorganism is administered, the obligate anaerobic microorganism may be administered in spore form. The obligate anaerobic microorganism may colonise the subject in a vegetative state following spore administration. The obligate anaerobic microorganism may colonise a tumour of the subject in a vegetative state following spore administration. The subject, such as a tumour of the subject, may be colonised by the obligate anaerobic microorganism in a vegetative state. In an embodiment or aspect of the invention wherein a subject is colonised with the obligate anaerobic microorganism, a tumour of the subject may be colonised by the obligate anaerobic microorganism. The subject, and/or a tumour thereof, may be colonised with the obligate anaerobic microorganism by intravenous administration of the obligate anaerobic microorganism. The subject, and/or a tumour thereof, may be colonised with the obligate anaerobic microorganism by injection of the obligate anaerobic microorganism directly into the tumour. The subject, and/or a tumour thereof, may be colonised with the obligate anaerobic microorganism by injection of spores of the obligate anaerobic microorganism directly into the tumour. The subject, and/or a tumour thereof, may be colonised with the obligate anaerobic microorganism by intravenous administration of spores of the obligate anaerobic microorganism. In one embodiment, a tumour of the subject may be colonised with the obligate anaerobic microorganism by administration of spores of the obligate anaerobic microorganism.

In an embodiment or aspect where the subject is administered or colonised with the obligate anaerobic microorganism, or spores thereof, the subject may be subsequently administered a prodrug activated by the polypeptide having nitroreductase activity. The subject, and\or tumour thereof, may be colonised, such as administered, with the obligate anaerobic microorganism, or spores thereof, prior to administration of the prodrug. The subject may be administered with the obligate anaerobic microorganism, or spores thereof, at least 12 hours prior to administration of the prodrug. The subject may be administered with the obligate anaerobic microorganism, or spores thereof, at least 6 hours prior to administration of the prodrug. The subject may be administered with the obligate anaerobic microorganism, or spores thereof, at least 1 day prior to administration of the prodrug. Alternatively, the subject may be administered with the obligate anaerobic microorganism, or spores thereof, at least 2 days prior to administration of the prodrug. The subject may be administered with the obligate anaerobic microorganism, or spores thereof, at least 3, 4 or 5 days prior to administration of the prodrug. The subject may be administered with the obligate anaerobic microorganism, or spores thereof, 5 days prior to administration of the prodrug.

Between about 5×10$^4$ and about 5×10$^9$ spores of the obligate anaerobic microorganism may be administered to the subject. Alternatively, between about 5×10$^6$ and about 5×10$^8$ spores of the obligate anaerobic microorganism may be administered to the subject. Between about 1×10$^7$ and about 1×10$^8$ spores of the obligate anaerobic microorganism may be administered to the subject. At least about 5×10$^7$ spores of the obligate anaerobic microorganism may be administered to the subject.

The subject may be a mammal. The subject may be a human, or non-human animal. In one embodiment, the subject is a human.

Nitroreductases are a family of evolutionarily related proteins involved in the reduction of nitrogen-containing compounds, including those containing the nitro functional group. Members of this family utilise FMN as a cofactor and are often found to be homodimers. Members of this family include oxygen-insensitive NAD(P)H nitroreductase (FMN-dependent nitroreductase) (6,7-dihydropteridine reductase) and NADH dehydrogenase. A number of these proteins are described as oxidoreductases. They are primarily found in bacterial lineages though a number of eukaryotic homologs have been identified.

The phrase "having nitroreductase activity" includes nitroreductase activity against CD1954. In particular, include the ability to reduce CB1954, preferably to a 4-hydroxylamine (4HX) derivative and/or a 2-hydroxylamine derivative (2HX). Nitroreductase activity against CB1954 can be determined using any suitable method known in the art. However, in an alternative or additional embodiment, nitroreductase activity against CB1954 is determined using the method described in the present Examples section, below.

The widely-studied *E. coli* NfnB which reduces CB1954 at either the 4-nitro group or 2-nitro group, producing equimolar quantities of the 4HX derivative and much less toxic 2-hydroxylamine (2HX) derivative (5-(aziridin-1-yl)-2-hydroxylamino-4-nitrobenzamide) (22, 23). It is preferred that the polypeptide of the present invention preferentially produces the 4HX derivative (i.e., produces more 4HX derivative than 2HX derivative). It is particularly preferred that the polypeptide of the present invention produces only the 4HX derivative.

Accordingly, the prodrug may comprise or consist of CB1954 (5-(aziridin-1-yl)-2,4-dinitrobenzamide) or its analogue SN 23862 5-(N,N-bis(2-chloroethyl)amino)-2,4-dinitrobenzamide). The drug active (i.e. the therapeutically active molecule converted from the prodrug) may comprise a 4-hydroxylamine (4HX) derivative of CB1954.

Reference to the polypeptide herein is intended to encompass the polypeptide having nitroreductase activity as provided in the method of the invention, in addition to the isolated polypeptide of the invention.

In one embodiment the polypeptide is capable of reducing CB1954 to the 4HX derivative with a $K_m$ of 25 micromolar or less, for example, 20 micromolar or less, 15 micromolar or less, 10 micromolar or less, 5 micromolar or less, 4.5 micromolar or less, 4 micromolar or less, 3.5 micromolar or less, 3 micromolar or less, 2.5 micromolar or less, 2 micromolar or less, 1 micromolar or less, 0.5 micromolar or less, or 0.25 micromolar or less. In one embodiment the polypeptide is capable of reducing CB1954 to the 4HX derivative with a $K_m$ of 6.3 micromolar or less.

In an alternative or additional embodiment the polypeptide is capable of reducing CB1954 to the 4HX derivative with a $K_m$ of 22 micromolar, for example, 22.03 micromolar. In an alternative or additional embodiment the polypeptide is capable of reducing CB1954 to the 4HX derivative with a $K_m$ of 2.5 micromolar, for example, 2.47 micromolar. In an alternative or additional embodiment the polypeptide is capable of reducing CB1954 to a 4-hydroxylamine (4HX) derivative substantially or wholly without producing the 2-hydroxylamine derivative (2HX).

In an alternative or additional embodiment the polypeptide comprises or consists of the amino acid sequence of:

a. SEQ ID NO: 1 (NmeNTR);

[SEQ ID NO: 1]
MTVLSKEQVLSAFKNRKSCRHYDAARKISAEDFQFILELGRLSPSSVG

SEPWQFIVVQNPEIRQAIKPFSWGMADALDIASHLVVFLAKKNARSDS

PFMLESLKRRGVTEPDAVAKSLARYQAFQADDIKILDDSRALFDWCCR

QTYIALANMMTGAAMAGIDSCPVEGFNYAEMERILSGQFGLFDAAEWG

VSVAATFGYRVQEIATKARRPLEETVIWA
NTR from *Neisseria meningitidis* MCS8 (NmeNTR)
or b. SEQ ID NO: 2 (HsoNTR);

[SEQ ID NO: 2]
MITISKEHVLDSFNRRASTRYYDPNKKISNEDFSYVLEFARLSPSSVG

SEPWHFLVIQNPELRAKLKPVSWGMATQIDDASHLVVILAKKNARYDS

EFLVQSMKRRGLSGEQIQATKEKYHLFQAEHMKTLENDRTLFDWASKQ

TYIALANMLTGAALIGIDSCPIEGFNYEKVNQILTDAGVLDSDEWGVS

VMATFGYRAKEIKPKSRKSLDEIVTWVK
NTR from *Haemophilus somnus* 129PT (HsoNTR)

or a fragment, variant or derivative thereof.

By "fragment" it is meant an incomplete portion of a protein, e.g., a naturally occurring protein or variant thereof.

By "variant" it is meant that the polynucleotide of the invention encodes a non-naturally occurring protein or fragment thereof. Thus, it includes insertions, deletions and substitutions, either conservative or non-conservative, where such changes do not substantially alter the immunogenicity of the polypeptide. By conservative substitutions is intended combinations such as Gly, Ala; Val, Ile, Leu; Asp, Glu; Asn, Gln; Ser, Thr; Lys, Arg; and Phe, Tyr. Such variants may be made using the well-known methods of protein engineering and site-directed mutagenesis.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (Thompson et al (1994) Nucl Acid Res 22, 4673-4680). The parameters used may be as follows:

Fast pairwise alignment parameters: K-tuple(word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

Methods of producing a polynucleotide of the invention are well known to those skilled in the art. Examples of such methods are discussed in Sambrook et al., *Molecular Cloning: A Laboratory Manual*, 2001, 3rd edition and also discussed in Examples below.

In an alternative or additional embodiment the polypeptide comprises or consists of the amino acid sequence of a fragment, variant or derivative of SEQ ID NO: 1. In a yet further alternative or additional embodiment the polypeptide comprises or consists of the amino acid sequence of a fragment, variant or derivative of SEQ ID NO: 2.

In a still furthermore alternative or additional embodiment the polypeptide is between 100 and 250 amino acids in length, for example, between 125 and 225 amino acids, for example, 221 amino acids in length. The polypeptide may be between 125 and 225 amino acids in length. The polypeptide may be 221 amino acids in length.

In an alternative or additional embodiment the polypeptide comprises or consists of a fragment of the amino acid sequence of SEQ ID NO: 1 or SEQ ID NO: 2, for example, the polypeptide may comprise or consist of at least 50 contiguous amino acids of SEQ ID NO: 1 or SEQ ID NO: 2, for example, 60, 70, 80, 90, 100, 110, 120, 130, 140, 150, 160, 170, 180, 190, 200, 210 or 220 contiguous amino acids of SEQ ID NO: 1 or SEQ ID NO: 2. The polypeptide may comprise or consist of at least 50 contiguous amino acids of SEQ ID NO: 1 or SEQ ID NO: 2. The polypeptide may comprise or consist of at least 200 contiguous amino acids of SEQ ID NO: 1 or SEQ ID NO: 2. The polypeptide may comprise or consist of at least 220 contiguous amino acids of SEQ ID NO: 1 or SEQ ID NO: 2.

In an alternative or additional embodiment the polypeptide comprises or consists of a variant of the amino acid sequence of SEQ ID NO: 1 or SEQ ID NO: 2, for example, the variant may share at least 20% sequence identify with the native polypeptide sequence, for example, at least 20%, 25%, 30%, 35%, 40%, 45%, 50%, 55%, 60%, 65%, 70% 75%, 80%, 85%, 90%, 95%, 96%, 97%, 98%, 99%, 99.5% or 99.75% sequence identity with the native polypeptide sequence. The polypeptide comprises or consists of a variant of the amino acid sequence of SEQ ID NO: 1 or SEQ ID NO: 2, for example, the variant may share at least 70% sequence identify with the native polypeptide sequence. The polypeptide comprises or consists of a variant of the amino acid sequence of SEQ ID NO: 1 or SEQ ID NO: 2, for example, the variant may share at least 80% sequence identify with the native polypeptide sequence. The polypeptide comprises or consists of a variant of the amino acid sequence of SEQ ID NO: 1 or SEQ ID NO: 2, for example, the variant may share at least 85% sequence identify with the native polypeptide sequence. The polypeptide comprises or consists of a variant of the amino acid sequence of SEQ ID NO: 1 or SEQ ID NO: 2, for example, the variant may share at least 90% sequence identify with the native polypeptide sequence. The polypeptide comprises or consists of a variant of the amino acid sequence of SEQ ID NO: 1 or SEQ ID NO: 2, for example, the variant may share at least 95% sequence identify with the native polypeptide sequence. The polypeptide comprises or consists of a variant of the amino acid sequence of SEQ ID NO: 1 or SEQ ID NO: 2, for example, the variant may share at least 98% sequence identify with the native polypeptide sequence.

In an alternative or additional embodiment the polypeptide comprises or consists of the amino acid sequence of SEQ ID NO: 1 or SEQ ID NO: 2, for example the polypeptide may consist of SEQ ID NO: 1; alternatively the polypeptide may consist of SEQ ID NO: 2.

By "isolated polynucleotide" it is meant that the polynucleotide is provided in a form and/or context distinct from that in which it is found in nature. In a preferred embodiment, the polynucleotide is a recombinant polynucleotide which may be inserted into a suitable expression vector and expressed in a suitable host cell (see below).

It will be appreciated by persons skilled in the art that the polynucleotide molecule of the invention may comprise or consist of DNA, RNA and synthetic oligonucleotides, as well as analogues, conjugates and derivatives thereof. Such nucleic acid molecules may be double-stranded or single-stranded. Preferably, however, the polynucleotide molecule is a DNA molecule.

Polynucleotide molecules of the invention may be made by methods well known to persons skilled in the art (see Sambrook & Russell, 2001, *Molecular Cloning: A Laboratory Manual*, Third Edition, Cold Spring Harbor Press, New York). For example, the nucleic acid molecules may be synthesised chemically or produced using a cloning vector.

The polynucleotide may comprise or consist of the nucleic acid sequence of:

a. SEQ ID NO: 3 (NmeNTR);

[SEQ ID NO: 3]
ATGACAGTATTAAGCAAAGAGCAGGTTCTATCCGCATTTAAAAACCGT

AAATCATGCCGGCATTACGATGCGGCACGCAAAATCAGTGCCGAGGAT

TTTCAGTTTATTTTAGAACTCGGGCGTTTGTCGCCCAGTTCGGTCGGT

TCGGAGCCTTGGCAGTTTATTGTGGTTCAAAACCCTGAAATCCGACAG

GCAATCAAGCCGTTTTCTTGGGGTATGGCGGATGCTTTGGATACCGCC

AGTCATTTGGTGGTGTTTTTGGCGAAGAAAAATGCCCGCTCCGACAGC

CCGTTTATGTTGGAAAGCCTCAAACGGCGCGGCGTTACCGAACCGGAT

GCCGTAGCAAAATCTTTGGCAAGGTATCAGGCGTTTCAAGCTGACGAC

ATCAAGATTTTGGACGATTCTCGCGCCTTGTTTGACTGGTGTTGCCGT

CAGACCTATATCGCGTTAGCCAACATGATGACGGGTGCGGCGATGGCA

GGTATCGATTCCTGCCCGGTGGAAGGTTTCAACTATGCCGAGATGGAG

CGCATATTGTCCGGGCAGTTTGGTTTGTTCGATGCGGCAGAATGGGGC

GTGTCCGTCGCCGCGACATTCGGCTACCGCGTTCAGGAAATCGCCACG

AAAGCGCGTAGGCCCTTGGAAGAAACCGTTATTTGGGCATAA
NTR from *Neisseria meningitidis* MCS8 (NmeNTR)
or b. SEQ ID NO: 4 (HsoNTR);

[SEQ ID NO: 4]
ATGACGACTATTTCAAAAGAACACGTGCTGGATAGTTTTAATCGTCGT

GCATCCACACGTTACTATGATCCAAATAAAAAAATCAGCAATGAAGAT

TTCTCTTATGTTTTGGAATTTGCTCGCCTTTCGCCAAGTTCTGTCGGC

TCTGAACCTTGGCATTTTTTAGTAATCCAAAATCCGGAACTACGGGCA

AAATTAAAACCTGTCAGCTGGGGAATGGCAACTCAAATTGACGATGCC

AGTCATTTAGTTGTTATCTTAGCGAAAAAGAATGCACGCTATGATTCA

GAATTTTTAGTACAATCCATGAAAAGACGTGGGTTATCCGGCGAACAA

ATACAAGCTACCAAAGAAAAATATCATCTCTTTCAAGCAGAACATATG

AAAACGCTTGAGAATGACCGCACTTTATTTGACTGGGCAAGTAAACAA

ACCTATATTGCCTTAGCAAATATGTTAACTGGTGCTGCATTAATTGGA

ATAGACAGTTGTCCAATTGAAGGTTTTAATTATGAAAAAGTAAATCAA

ATTTTAACTGACGCAGGTGTATTAGATTCAGA(GAATGGGAGTTTCG

```
                            -continued
GTAATGGCAACTTTCGGCTACCGAGCAAAAGAAATTAAGCCAAAATCC CGTAAATCCCTTGATGAAATCGTCACTTGGGTTAAATAA
NTR from Haemophilus somnus 129PT (HsoNTR)
``` or a fragment or variant thereof.

In an alternative or additional embodiment the polynucleotide comprises or consists of a nucleic acid sequence of between 300 and 750 nucleic acids in length, for example, between 375 and 675 nucleic acids, between 450 and 666 nucleic acids, or between 450 and 600 nucleic acids in length. In an alternative or additional embodiment the polynucleotide comprises or consists of a nucleic acid sequence of between 450 and 600 nucleic acids in length.

In an alternative or additional embodiment the polynucleotide comprises or consists of a polynucleotide sequence of 666 nucleic acids in length.

In an alternative or additional embodiment the polynucleotide comprises or consists of a fragment of the nucleic acid sequence of SEQ ID NO: 3 or SEQ ID NO: 4. The fragment may comprise or consist of at least 150 contiguous nucleic acids of SEQ ID NO: 1 or SEQ ID NO: 2, for example, 180, 210, 240, 270, 300, 330, 360, 390, 420, 450, 480, 510, 540, 570, 600, 630, 660 or 663 contiguous nucleic acids of SEQ ID NO: 3 or SEQ ID NO: 4. The fragment may comprise or consist of at least 150 contiguous nucleic acids of SEQ ID NO: 1 or SEQ ID NO: 2. The fragment may comprise or consist of at least 300 contiguous nucleic acids of SEQ ID NO: 1 or SEQ ID NO: 2 The fragment may comprise or consist of at least 600 contiguous nucleic acids of SEQ ID NO: 1 or SEQ ID NO: 2. The fragment may comprise or consist 663 contiguous nucleic acids of SEQ ID NO: 1 or SEQ ID NO: 2

In an alternative or additional embodiment the polynucleotide comprises or consists of a variant of the nucleic acid sequence of SEQ ID NO: 3 or SEQ ID NO: 4. The variant may share at least 20% sequence identify with the native polynucleotide sequence, for example, at least 25%, 30%, 35%, 40%, 45%, 50%, 55%, 60%, 65%, 70% 75%, 80%, 85%, 90%, 95%, 96%, 97%, 98%, 99%, 99.5% or 99.75% sequence identity with the native polypeptide sequence. The variant may share at least 60% sequence identify with the native polynucleotide sequence. The variant may share at least 70% sequence identify with the native polynucleotide sequence. The variant may share at least 80% sequence identify with the native polynucleotide sequence. The variant may share at least 85% sequence identify with the native polynucleotide sequence. The variant may share at least 90% sequence identify with the native polynucleotide sequence. The variant may share at least 95% sequence identify with the native polynucleotide sequence. The variant may share at least 98% sequence identify with the native polynucleotide sequence.

In an alternative or additional embodiment the codon usage of the polynucleotide has been optimised (i.e., the nucleic acid sequence has been codon optimised).

It will be appreciated by persons skilled in the art that each amino acid making up a gene sequence can be encoded by several different codons. The use of particular codons for any amino acid is not random in most cases and appears to be species specific, with each species showing a particular codon bias (see Sharp & Li, 1987, Nucleic Acids Res 15(3):1281-95). When expressing a protein it is possible to produce a synthetic sequence by substituting wild-type codons for ones that are optimised for the organism in which the gene is to be expressed, thereby increasing gene expression in the host.

Thus, "codon optimised", "the codon usage of the polynucleotide has been optimised" or "optimised for protein expression" includes that the polynucleotide molecule comprises or consists of a nucleotide sequence wherein some or all of the codons present in the gene sequence are replaced with codons which encode the same amino acid but are more commonly found in the genes of the intended host organism. The codons may be optimised for expression of the microorganism as defined in the invention.

Methods of codon optimisation are well known in the art, for example the Upgene and Codon Optimizer software, as described in Gao et al., 2004, *Biotechnol Prog.* 20(2):443-8 and Fuglsang, 2003, *Protein Expr Purif.* 31(2):247-9. Alternative codon optimisation resources include JCat (see Nucleic Acid Research, 2005, 33:W526-531) and Synthetic Gene Designer (see www.evolvingcode.net/codon/sgd/index.php).

Thus, "codon optimised", "the codon usage of the polynucleotide has been optimised" or "optimised for protein expression" includes that the codon usage of the polynucleotide has been altered in order to maximise the amount of protein expressed in the intended expression background (e.g., host organism), in particular, the amount of functional and, preferable, soluble protein expressed.

In an alternative or additional embodiment, the polynucleotide of the invention is optimised for heterologous expression (i.e., expression in an organism other than the one it originated or was derived from). The polynucleotide may be codon optimised for heterologous protein expression.

As mentioned above, a key area of application for the polypeptide and polynucleotides of the present invention is Directed Enzyme Prodrug Therapy (DEPT). DEPT uses enzymes artificially introduced into the body to convert prodrugs, which have no or poor biological activity, to the active form in the desired location within the body. Many chemotherapy drugs for cancer lack tumour specificity and the doses required to reach therapeutic levels in the tumour are often toxic to other tissues. DEPT strategies are an experimental method of reducing the systemic toxicity of a drug, by achieving high levels of the active drug only at the desired site.

Clostridia-directed enzyme prodrug therapy (CDEPT) uses Clostridia to convert prodrugs into active drug agents. CDEPT exploits the hypoxic environments (in particular, those of solid tumours) to target drugs to tumours using anaerobic bacteria resident in the tumour to convert the pro-drug to the active form. Intravenously injected clostridial spores exhibit a specificity for tumours, colonising the hypoxic areas of the tumours.

Perhaps the most challenging issue in cancer treatment is how to reduce the side effects of the injected anti-cancer agents, which are of a high cytotoxicity potential. A widely used solution is to use enzymes which are able to convert a relatively non-toxic prodrug precursor into the active drug form(s).

Solid tumours, in contrast to normal tissues, grow rapidly. As a result, the cancerous tissues may suffer from inadequate blood and oxygen supply. Therefore, clostridia can grow in tumour and destroy it specifically. Originally, Parker et al., (1947 "Effect of histolyticus infection and toxin on transplantable mouse tumours". *Proc. Soc. Exp. Biol. Med.* 66: 461-5) showed that the injection of *Clostridium histolyticum* spores to the transplanted sarcomas of mice results in significant tumour lysis. Soon after, it was shown that a direct injection is not necessary, and that tumour colonization was readily obtained after intravenous administration of spores (Malmgren & Flanigan, 1955, "Localization of the vegetative form of *Clostridium tetani* in mouse tumours following intravenous spore administration". *Cancer Res.* 15 (7): 473-8).

In CDEPT, a prodrug-converting enzyme expressed by a clostridial expression plasmid converts a prodrug into an active drug form within the tumour. While the prodrug is the inactive form and can be administered to the blood, the products of the prodrug cleavage are highly cytotoxic and show their effect only in the vicinity of tumour cells.

Difficulties in the engineering of clostridial strains have restricted the application of other enzyme prodrug systems. So far, two enzymes have been applied in CDEPT: cytosine deaminase and nitroreductase.

In an alternative or additional embodiment, the polynucleotide of the invention is optimised for heterologous expression. Accordingly, in an alternative or additional embodiment, it is preferred that the polynucleotide has been optimised for heterologous expression in a microorganism that is an obligate *anaerobe*.

Generally, the polynucleotide is inserted into an expression vector, such as a plasmid, in proper orientation and correct reading frame for expression. If necessary, the polynucleotide, e.g. DNA, may be linked to the appropriate transcriptional and translational regulatory control nucleotide sequences recognised by the desired host, although such controls are generally available in the expression vector. Thus, the polynucleotide insert may be operatively linked to an appropriate promoter. The expression constructs will desirably also contain sites for transcription initiation and termination, and in the transcribed region, a ribosome-binding site for translation (see WO 98/16643).

Methods well known to those skilled in the art can be used to construct expression vectors containing the coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or *E. coli* DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al. (1988) *Science* 239, 487-491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Cellular respiration (both aerobic and anaerobic) utilizes highly reduced species such as NADH and FADH2 (for example produced during glycolysis and the citric acid cycle) to establish an electrochemical gradient (often a proton gradient) across a membrane, resulting in an electrical potential or ion concentration difference across the membrane. The reduced species are oxidized by a series of respiratory integral membrane proteins with sequentially increasing reduction potentials with the final electron acceptor being oxygen (in aerobic respiration) or another species (in anaerobic respiration). The membrane in question is the inner mitochondrial membrane in eukaryotes and the cell membrane in prokaryotes. A proton motive force or pmf drives protons down the gradient (across the membrane) through the proton channel of ATP synthase. The resulting current drives ATP synthesis from ADP and inorganic phosphate.

Fermentation in contrast, does not utilize an electrochemical gradient. Fermentation instead only uses substrate-level phosphorylation to produce ATP. The electron acceptor NAD+ is regenerated from NADH formed in oxidative steps of the fermentation pathway by the reduction of oxidized compounds. These oxidized compounds are often formed during the fermentation pathway itself, but may also be external. For example, in homofermentative lactic acid bacteria, NADH formed during the oxidation of glyceraldehyde-3-phosphate is oxidized back to NAD+ by the reduction of pyruvate to lactic acid at a later stage in the pathway. In yeast, acetaldehyde is reduced to ethanol.

The term "obligate *anaerobe*" includes organisms with a fermentation or anaerobic respiration metabolism, lacking an aerobic metabolism, the growth and/or viability of which is reduced or abolished by the presence of oxygen (e.g., $O_2$).

The obligate *anaerobe* microorganism may be capable of sporulation. The obligate *anaerobe* microorganism may be a bacterium.

In an alternative or additional embodiment the microorganism is a bacterium of the class Clostridia.

The Clostridia are a highly polyphyletic class of Firmicutes, including *Clostridium* and other similar genera. They are distinguished from the Bacilli by lacking aerobic respiration. They are obligate *anaerobes* and oxygen is toxic to them. Species of the genus *Clostridium* are all Gram-positive and have the ability to form spores. Studies show they are not a monophyletic group, and their relationships are not entirely certain. Currently most are placed in a single order called Clostridiales, but this is not a natural group and is likely to be redefined in the future.

Most species of the genus *Clostridium* are saprophytic organisms found in many places in the environment, most notably the soil. However, the genus does contain some human pathogens (outlined below). The toxins produced by certain members of the *Clostridium* genus are among the most dangerous known. Examples are tetanus toxin (known as tetanospasmin) produced by *C. tetani* and botulinum toxin produced by *C. botulinum*.

Notable species of this class include: *Clostridium perfringens; Clostridium difficile; Clostridium tetani; Clostridium botulinum; Clostridium acetobutylicum; Clostridium hae-*

*molyticum; Clostridium novyi*; and *Clostridium oedematiens*. Heliobacteria are also members of the class Clostridia.

In an alternative or additional embodiment the microorganism is a bacterium of the order Clostridiales. In an alternative or additional embodiment the microorganism is a bacterium of the family Clostridiacae. In an alternative or additional embodiment the microorganism is a bacterium of the genus *Clostridium*. Thus, the Clostridial species may be selected from the group consisting of:
  a. *Clostridium sporogenes*; and
  b. *Clostridium novyi*.

Thus, the Clostridial species may be selected from the group consisting of:
  a. *Clostridium sporogenes* NCIMB 10696; and
  b. *Clostridium novyi* NT.

The vector of the invention may be a protein expression vector. The vector may be suitable for protein expression in a microorganism. The microorganism may be a microorganism as defined in respect of the invention.

The expression system may be located in the chromosome or localised to an extrachromosomal element/vector or a combination thereof (e.g., an autonomous plasmid). The vector may be a chromosomal integration vector (i.e., is not an autonomous plasmid).

In an alternative or additional embodiment, the expression system is an 'orthogonal' expression system. The expression system may be 'orthogonal' for transcription or translation, but is preferably 'orthogonal' for both transcription and translation.

The concept of 'orthogonal' expression systems is being explored by researchers in synthetic biology, and potentially offers high level expression as discussed in An and Chin, 2009, *Proc Natl Sci USA* 106: 8477-82. Orthogonal systems are uncoupled from evolutionary constraints, and selectively abstracted from cellular regulation, making use of heterologous elements, such as phage T7 polymerase. The advantage of using such polymerases resides in the fact that they are specifically targeted to the promoter employed in front of the transgene.

In an alternative or additional embodiment, the expression system is an 'orthogonal' expression system utilising group 5 RNA polymerase sigma factors (which include BotR, TetR, TcdR and UviA) such as the expression system described in International publication number WO 2013/144647.

Recombination is the production of new DNA molecule(s) from two parental DNA molecules or different segments of the same DNA molecule. Transposition is a highly specialized form of recombination in which a segment of DNA moves from one location to another on a chromosome.

Conditional vectors are a pivotal tool in the genetic manipulation of bacterial strains, such vectors only replicate and are maintained during cell growth under a permissive condition. Under a non-permissive condition, their replicative maintenance in the cell is curtailed. This facility makes them ideal vehicles for a number of purposes.

Conditional vectors may be used in the delivery of transposable elements. Thus, a conditional vector carrying a transposable element is first introduced into a bacterial cell by either conjugation or transformation and the transconjugants/transformants selected under the permissive condition. The cells are then grown under the non-permissive condition during which selection is imposed for the presence of the transposon, typically where the transposon carries a gene encoding for antibiotic resistance, and the media is supplemented with an appropriate antibiotic. As the plasmid can no longer replicate, antibiotic resistant progeny can only arise if the transposon has inserted into a non-essential region of the host bacterial genome.

One of the most common forms of a conditional vector is a vector that is only stably maintained under a permissive temperature e.g., 30° C. and is not able to replicate at a higher, non-permissive temperature, e.g., 42° C. This can be a consequence of the temperature instability of a key component of the replication machinery, such as the replication protein or an essential RNA component that does not fold appropriately at the non-permissive temperature.

In an alternative or additional embodiment the transposon system developed for *Clostridium difficile* described in Cartman S T and Minton N P, 2010, *Applied Environmental Microbiology*, 76: 1103-1109 is employed. It consists of a mini-transposon in which the selectable marker catP (resistance to thiamphenicol/chloramphenicol) is flanked by inverted repeat regions (ITR1 & ITR2), proceeded by the transposase gene. Transposition is by a 'cut and paste' mechanism—the transposase 'cuts' out the mini-transposon at ITR1/ITR2, and then 'pastes' it into the genome at random at any 'TA' di-nucleotide.

In an alternative or additional embodiment the transposon system described in WO 2013/144653 is employed.

Recombinant DNA technology uses two other types of recombination. The directed cutting and rejoining of different DNA molecules in vitro using restriction endonucleases and DNA ligases is well-known. Once made, these recombinant DNA molecules are then introduced into a host organism, often a bacterium. If the recombinant DNA is a plasmid, phage or other molecule capable of replicating in the host, it will stay extrachromosomal. However, one can introduce the recombinant DNA molecule into a host in which it cannot replicate. In order for the host to be stably transformed, the introduced DNA has to be taken up into a host chromosome. In bacteria and yeast, this can occur by homologous recombination at a reasonably high frequency. Thus random recombination into chromosomes can make stably transfected cells.

DNA can be added to microorganisms using replicative plasmids, but these are inherently unstable, limiting their applied utility. To stabilize exogenous DNA, it must be irreversibly incorporated into a stable DNA molecule inside the cell, usually a chromosome. This can be accomplished in a one-step homologous recombination procedure (often called 'allele exchange' or 'gene replacement') for those organisms that are efficiently transformed with linear DNA, such as yeast and naturally competent bacteria like *Bacillus subtilis*. A selectable marker gene positioned alongside the DNA sequence of interest within an allele exchange cassette is only retained by the desired recombinant cells, allowing these cells to be specifically selected and easily isolated, typically using an antibiotic. Large or multiple sequences can be inserted at a single locus simply by alternating between two selectable markers in a series of integration steps, as in the 'domino' method of Itaya et al.

Most bacteria cannot be transformed with linear DNA, so an integrative plasmid bearing the homologous recombination construct is used instead. As plasmids are circular, a single homologous recombination event can reversibly integrate the entire plasmid into the chromosome, resulting in unstable single-crossover cells with the potential to revert to wild-type. The desired stable double-crossover cells are much rarer, as they result from two homologous recombination events in a single cell or lineage. Double-crossover cells are not easily isolated from single-crossover cells, because both contain the selectable marker in the cassette.

This issue can be overcome using a counter-selection marker located on the plasmid 'backbone', but identifying a suitable counter-selection marker and appropriate conditions for its use can be one of the most challenging aspects of developing genetic tools for a particular organism.

In an alternative or additional embodiment, the vector according to the invention may be a chromosomal insertion vector (introducing DNA via a single crossover event) or a chromosomal replacement vector (introducing DNA via a double crossover event).

In an alternative or additional embodiment the vector is a chromosomal insertion vector suitable for use in a method selected from the group consisting of:
a. mobile group II intron insertion, such as ClosTron; and
b. allele coupled exchange.

In an alternative or additional embodiment the vector is capable of rendering the host organism auxotrophic for one or more nutrient, for example, uracil.

In an alternative or additional embodiment the vector is capable of deactivating a pyrE and/or pyrF gene(s). The vector may be capable of deactivating a pyrE gene. In an alternative or additional embodiment the vector is pMTL-JH27 (GenBank Accession number HQ875763), the construction and use of which is described in Heap et al. (2012) Integration of DNA into bacterial chromosomes from plasmids without a counter-selection marker. *Nucl Acids Res* 40(8):e59.

The host cell of the invention may be an obligate anaerobic microorganism. The obligate anaerobic microorganism may encode and/or express the polypeptide having nitroreductase activity, wherein the polypeptide: exhibits preferential reduction of CB1954 to a 4-hydroxylamine (4HX) derivative instead of a 2-hydroxylamine derivative; and is capable of reducing CB1954 to the 4HX derivative with a $K_m$ of less than 30 micromolar. The polypeptide defined in the invention may be heterologous to the host cell. The host cell may comprise a polynucleotide according to the invention and/or a vector according to the invention. In an alternative or additional embodiment, the polynucleotide according to the invention and/or a vector according to the invention is operably integrated into the chromosome of the host cell. The integration may be via a single recombination event or a double recombination event but is preferably via a double recombination event.

In an alternative or additional embodiment, the host cell is a microorganism, such as an obligate anaerobic microorganism as defined in respect of the invention. In an alternative or additional embodiment, the host cell is auxotrophic for one or more nutrient, such as an essential nutrient (for example, as described in relation to the invention). The obligate anaerobic microorganism may be auxotrophic for an essential amino acid or nucleobase. The obligate anaerobic microorganism may be auxotrophic for uracil. The obligate anaerobic microorganism may comprise a deactivated pyrE and/or pyrF gene(s). In an alternative embodiment, the obligate anaerobic microorganism may not express from, or comprise, a functional pyrE and/or pyrF gene(s). In an additional or alternative embodiment, the microorganism is provided in the form of spores.

The obligate anaerobic microorganism may not comprise an exogenous antibiotic resistance gene. The obligate anaerobic microorganism may not comprise a gene for resistance to erythromycin or thiamphenicol, or combinations thereof.

As used herein, 'pharmaceutical composition' means a therapeutically effective formulation according to the invention.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent.

In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

The agents, medicaments and pharmaceutical compositions of the invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period. Delivery may be performed intra-muscularly (i.m.) and/or subcutaneously (s.c.) and/or intravenously (i.v.).

The agents, medicaments and pharmaceutical compositions of the invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of the agents, medicaments and pharmaceutical compositions of the invention. A device which delivers a pulsed electric field to cells increases the permeability of the cell membranes to the drug, resulting in a significant enhancement of intracellular drug delivery.

The agents, medicaments and pharmaceutical compositions of the invention can also be delivered by electro-incorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of delivery of the agents, medicaments and pharmaceutical compositions of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The agents, medicaments and pharmaceutical compositions of the invention can also be delivered orally. The process employs a natural process for oral uptake of vitamin $B_{12}$ and/or vitamin D in the body to co-deliver proteins and peptides. By riding the vitamin $B_{12}$ and/or vitamin D uptake system, the agents, medicaments and pharmaceutical compositions of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The agents, medicaments and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), Trends Cell Biol 8, 84-87.

The medicaments and/or pharmaceutical compositions of the present invention may be a unit dosage containing a daily dose or unit, daily sub-dose or an appropriate fraction thereof, of the active ingredient.

The agents, medicaments and pharmaceutical compositions of the invention will normally be administered orally or by any parenteral route, in the form of a pharmaceutical composition comprising the active ingredient(s), optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agents, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the agents, medicaments and pharmaceutical compositions of the invention can be administered orally, buccally or sublingually in the form of capsules, ovules, elixirs, solutions or suspensions, which may contain flavouring or colouring agents, for immediate-, delayed- or controlled-release applications. The agents, medicaments and pharmaceutical compositions of the invention may also be administered via intracavernosal injection.

The liquid compositions of the invention may also be employed as fillers in gelatin capsules. Preferred excipients in this regard include lactose, starch, cellulose, milk sugar or high molecular weight polyethylene glycols. For aqueous suspensions and/or elixirs, the agents, medicaments and pharmaceutical compositions of the invention may be combined with various sweetening or flavouring agents, colouring matter or dyes, with emulsifying and/or suspending agents and with diluents such as water, ethanol, propylene glycol and glycerin, and combinations thereof.

The agents, medicaments and pharmaceutical compositions of the invention can be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (for example to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and pharmaceutical compositions may be presented in unit-dose or multi-dose containers, for example sealed ampoules and vials.

For oral and parenteral administration to human patients, the daily dosage level of the agents, medicaments and pharmaceutical compositions of the invention will usually be from 5 to 1500 mg per adult per day administered in single or divided doses.

Thus, for example, the agents, medicaments and pharmaceutical compositions of the invention may contain from 5 mg to 1400 mg (for example, from 7 mg to 1400 mg, or 5 mg to 1000 mg) and may contain 5 mg to 200 mg of active agent for administration singly or two or more at a time, as appropriate.

In one embodiment, the agents, medicaments and pharmaceutical compositions of the invention are administered at a dosage ranging from 0.02 mg/kg to 2 mg/kg and at a frequency ranging from twice per week to once per month.

The prodrug may be administered at a dose of at least 1 mg/kg. The prodrug may be administered at a dose of at least 2 mg/kg. The prodrug may be administered at a dose of at least 3 mg/kg. The prodrug may be administered at a dose of at least 5 mg/kg. The prodrug may be administered at a dose of at least 10 mg/kg. The prodrug may be administered at a dose of at least 15 mg/kg. The prodrug may be administered at a dose of at least 20 mg/kg. Alternatively, the prodrug may be administered at a dose of at least 25 mg/kg. The prodrug may be administered at a dose of between about 2 mg/kg and about 50 mg/kg. The prodrug may be administered at a dose of between about 2 mg/kg and about 30 mg/kg. The prodrug may be administered at a dose of between about 2 mg/kg and about 20 mg/kg. The prodrug may be administered at a dose of between about 2 mg/kg and about 10 mg/kg. The prodrug may be administered at a dose of between about 2 mg/kg and about 30 mg/kg. The prodrug may be administered at a dose of between about 5 mg/kg and about 30 mg/kg. The prodrug may be administered at a dose of between about 10 mg/kg and about 30 mg/kg. The prodrug may be administered at a dose of between about 15 mg/kg and about 30 mg/kg. The prodrug may be administered at a dose to provide a concentration of 6.3 µM, or less in the subject's serum.

The agents, medicaments and pharmaceutical compositions of the invention can also be administered intranasally or by inhalation and are conveniently delivered in the form of an inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of an agent of the invention and a suitable powder base such as lactose or starch.

Aerosol or inhaled formulations may be arranged so that each metered dose or "puff" contains at least 1 mg of an agent of the invention for delivery to the patient. It will be appreciated that he overall daily dose with an aerosol will vary from patient to patient, and may be administered in a single dose or, more usually, in divided doses throughout the day.

Alternatively, the agents, medicaments and pharmaceutical compositions of the invention can be administered in the form of a suppository or pessary, or they may be applied topically in the form of a lotion, solution, cream, gel or ointment. The agents, medicaments and pharmaceutical compositions of the invention may also be transdermally administered, for example, by the use of a skin patch. They may also be administered by the ocular route, particularly for treating diseases of the eye.

For ophthalmic use, the agents, medicaments and pharmaceutical compositions of the invention can be formulated as micronised suspensions in isotonic, pH adjusted, sterile saline, or, as solutions in isotonic, pH adjusted, sterile saline, optionally in combination with a preservative such as a benzylalkonium chloride. Alternatively, they may be formulated in an ointment such as petrolatum.

For application topically to the skin, the agents, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the agents, medicaments and pharmaceutical compositions of the invention is the preferred route, being the most convenient.

For veterinary use, the agents, medicaments and pharmaceutical compositions of the invention are administered as a suitably acceptable formulation in accordance with normal veterinary practice and the veterinary surgeon will determine the dosing regimen and route of administration which will be most appropriate for a particular animal.

The agents of the invention may be formulated at various concentrations, depending on the efficacy/toxicity of the compound being used, for example as described in the accompanying Examples. For in vitro applications, formulations may comprise a lower concentration of a compound of the invention.

Thus, the present invention provides a pharmaceutical composition comprising an amount of a protein-agent conjugate of the invention effective to treat various conditions (as described above and further below).

The composition or prodrug may be for delivery parenterally (for example, intravenously, intraarticularly, intraarterially, intraperitoneally, intrathecally, intraventricularly, intrasternally, intracranially, intramuscularly or subcutaneously), intranasally, by inhalation or intraocularly. The prodrug, or a pharmaceutical composition comprising the prodrug, may be administered intravenously.

The present invention also includes pharmaceutical compositions comprising pharmaceutically acceptable acid or base addition salts of the polypeptide binding moieties of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the agents according to the present invention.

The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

In one embodiment the polypeptide, polynucleotide, vector, host cell or pharmaceutical composition is for use in treating solid tumours.

The cancer may be a solid tumour cancer. In an alternative or additional embodiment, the solid tumour is selected from the group consisting of Adrenocortical Carcinoma, Carcinomas, Colorectal Carcinoma, Desmoid Tumors, Desmoplastic Small Round Cell Tumor, Endocrine Tumors, Ewing Sarcoma Family Tumors, Germ Cell Tumors (Solid Tumor), Hepatoblastoma, Hepatocellular Carcinoma, Melanoma, Neuroblastoma, Non-Rhabdomyosarcoma Soft Tissue Sarcoma (NRSTS), Osteosarcoma, Retinoblastoma, Rhabdomyosarcoma and Wilms Tumor.

In an alternative or additional embodiment, the solid tumour is present in and/or derived from the group of organs selected from the group consisting of heart, arteries, veins, capillaries, cisterna chyli, spleen, thoracic duct, right lymphatic duct, lymph vessels, tonsils, adenoids, thymus, lymph nodes, tongue, salivary glands, esophagus, stomach, liver, gallbladder, pancreas, small intestine, large intestine, rectum, anus, hypothalamus, pituitary gland, pineal body, thyroid gland, parathyroids, suprarenal glands, skin, mammary glands, breast, individual muscles of the body, brain, spinal cord, peripheral nerves, ovaries, fallopian tubes, uterus, clitoris, vagina, testes, vas deferens, seminal vesicles, prostate, penis, pharynx, larynx, trachea, bronchi, lungs, diaphragm, Bone marrow, kidneys, ureters, bladder, urethra, eyes, olfactory bulbs, vomeronasal organ, vestibulocochlear organ, and taste buds of the tongue.

The polypeptide, polynucleotide, vector, host cell or pharmaceutical composition of the invention may for use in combination with a prodrug capable of being converted to drug by a polypeptide according to the invention. The prodrug may be selected from the group consisting of:
  a. CB1954; and
  b. SN 23862.

As used herein, the singular forms "a", "and", and "the" include plural referents unless the context clearly dictates otherwise. Thus, for example, reference to "the dosage" includes reference to one or more dosages and equivalents thereof known to those skilled in the art, and so forth.

The skilled person will understand that optional features of one embodiment or aspect of the invention may be applicable, where appropriate, to other embodiments or aspects of the invention.

The listing or discussion in this specification of an apparently prior-published document should not necessarily be taken as an acknowledgement that the document is part of the state of the art or is common general knowledge.

Preferred, non-limiting examples which embody certain aspects of the invention will now be described, with reference to the following figures:

FIG. 1: The 'prodrug' CB1954 is a low-toxicity monofunctional DNA alkylating agent, but can be converted to a much more toxic bifunctional DNA alkylating agent upon 2×2-electron reduction of the 4-nitro or 2-nitro group to the corresponding hydroxylamine. The 4-hydroxylamine is more cytotoxic than the 2-hydroxylamine. Some NAD(P)H-dependent nitroreductase (NTR) enzymes can catalyse this reaction, with varying kinetics and nitro group specificity (see Table 1).

Figure 2:
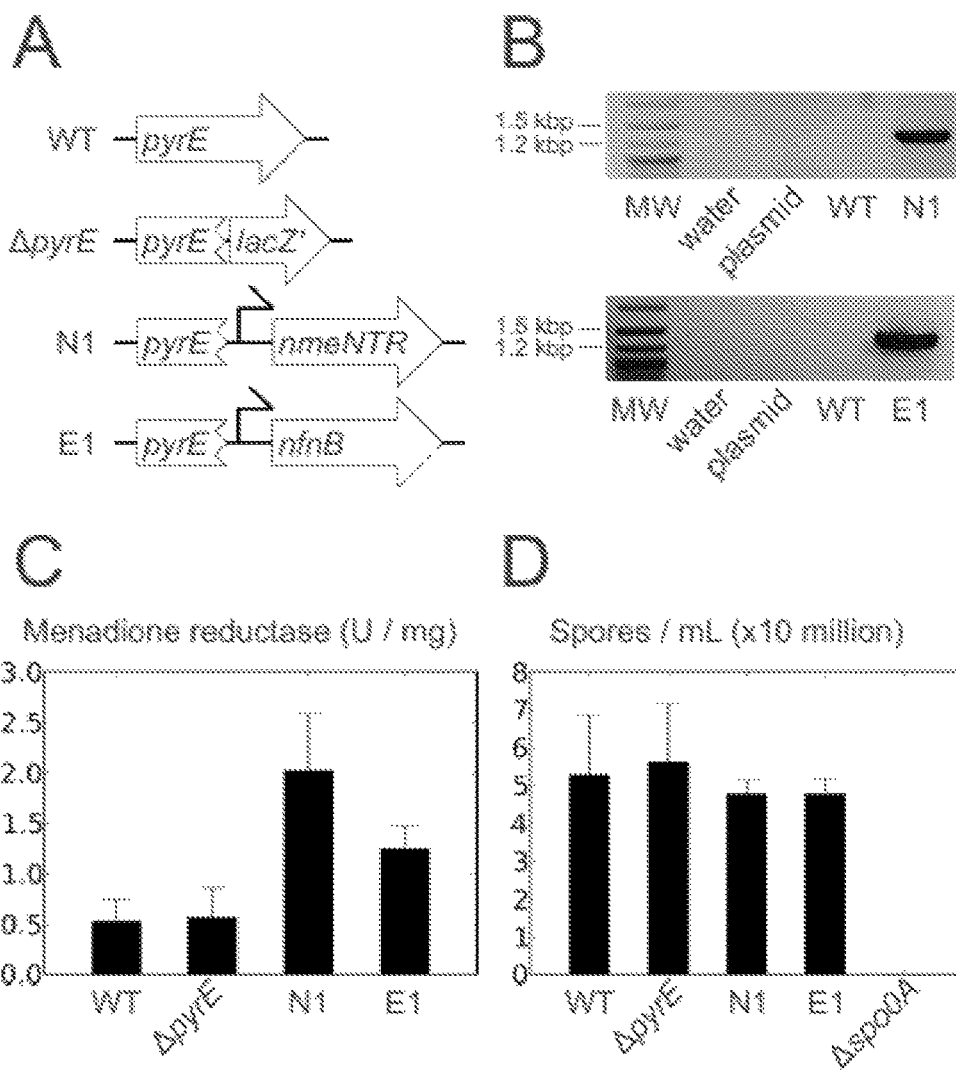

FIG. 2: Construction and in vitro characterisation of *C. sporogenes* therapeutic strains. (A) Chromosomal pyrE locus of therapeutic strains and control strains. WT, wild-type; ΔpyrE, a mutant constructed previously by integrating the 'empty' cloning site (lacZ') of pMTL-JH27 (32); N1, the strain containing a NmeNTR expression cassette; E1, the strain containing an *E. coli* NfnB expression cassette; angled arrows, fdx promoter. (A) Successful integration shown by PCR using chromosome-specific primer Csp-pyrD-sF2 in combination with insert-specific primer M13F. MW, 2-Log DNA Ladder (NEB) molecular weight marker; plasmid, pMTL-JH27 derivative containing NmeNTR or NfnB cassette accordingly; WT, wild-type *C. sporogenes* genomic DNA; N1 and E1, genomic DNA from strain N1 or E1 respectively. (C) Functional expression of NmeNTR and NfnB, in strains N1 and E1 respectively, indicated by specific menadione reductase activities in cell lysates. Data shown are the mean of three independent experiments, error bars show standard deviation. N1 and E1 show specific menadione reductase activities elevated above the background activity of endogenous quinone reductases seen in WT and ΔpyrE. (D) NTR-expressing and control strains are equally able to form spores. Strains were grown in complex medium (TYG) for five days, heated to inactivate vegetative cells, and spore titres were determined by plating. A non-sporulating Δspo0A mutant constructed previously (30) is included as a control. Data shown are the mean of three independent experiments, error bars show standard deviation.

Figure 3:
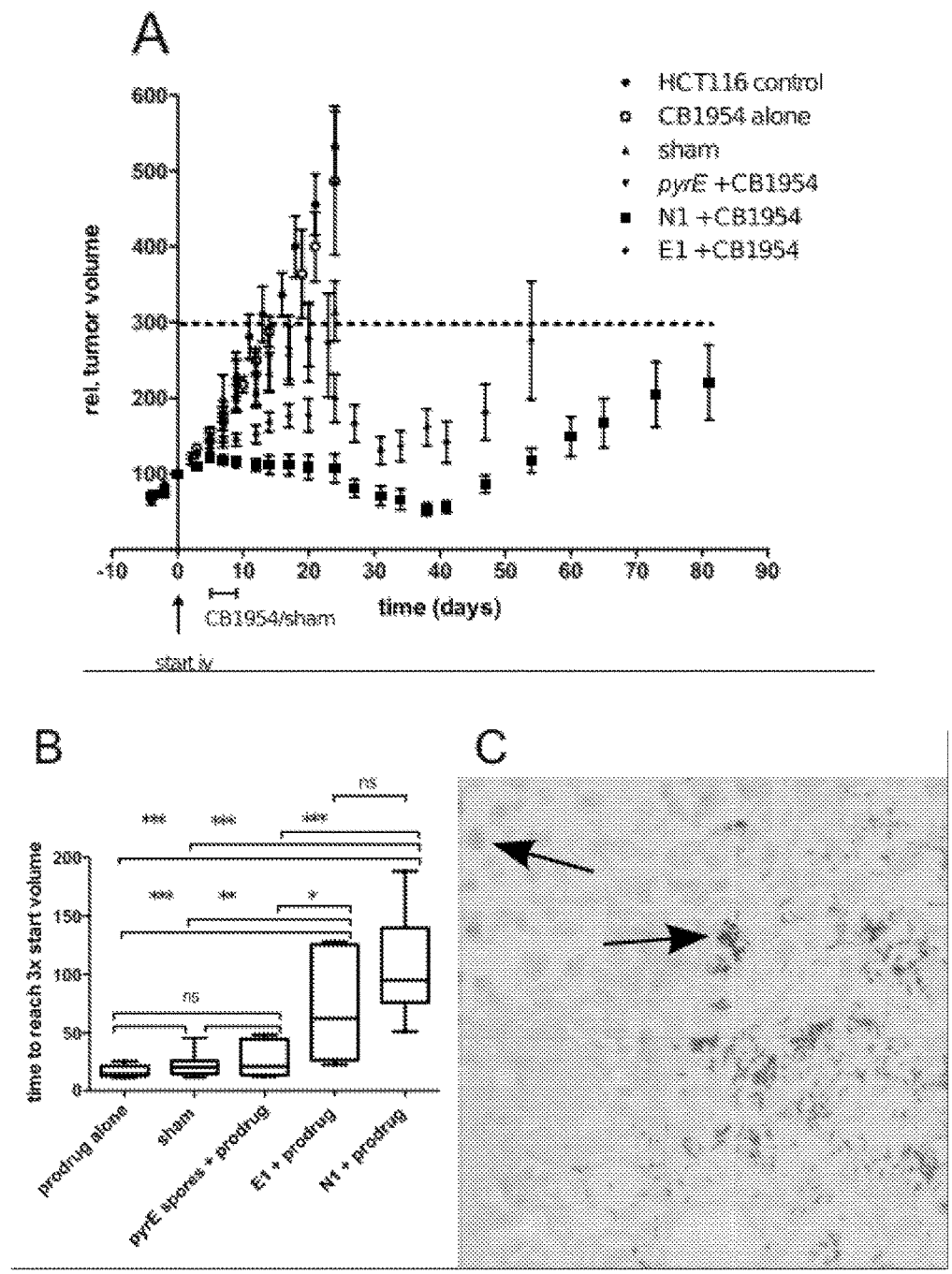

FIG. 3: The NTR-expressing therapeutic strains are efficacious in CB1954 therapy in vivo. (A) Growth curves of HCT116 tumours treated as indicated in the legend. Spores ($5 \times 10^7$) were injected on day 0 when tumours reached a volume of ~250 mm³ and CB1954 prodrug (15 mg/kg) or sham treatment was given for 5 consecutive days starting at day 5 post spore injection. Data shown are average±SEM. (B) Growth delay of individual tumours in the different groups. Growth delay is defined as the time for the tumour to reach three times its volume at the start of the prodrug or sham treatment. Statistical differences between different groups are calculated using the non-parametric Mann-Whitney test (*, $p<0.05$; **, $p<0.01$; *, $p<0.001$) (C) Representative Gram staining of tumour sections showing colonization of the tumour by *C. sporogenes* vegetative cells following spore administration, germination in the tumour, and outgrowth. *C. sporogenes* vegetative cells are visible as Gram-positive purple rods and reside in the necrotic area of the tumour. HCT116 nuclei (pink) are counterstained with iodine solution.

Table 1: CB1954 nitroreductase properties of selected enzymes.

The enzymes shown include those with the most favourable values reported for $K_{cat}$, $K_m^{CB1954}$, and $K_{cat}/K_m^{CB1954}$.

EXAMPLES

Introduction

Spores of some species of the strictly anaerobic bacteria *Clostridium* naturally target and partially lyse the hypoxic cores of solid tumours, which tend to be refractory to conventional therapies. The anti-tumour effect can be augmented by engineering strains to convert a non-toxic 'prodrug' into a cytotoxic drug specifically at the tumour site by expressing a prodrug-converting enzyme (PCE). Safe doses of the favoured prodrug CB1954 lead to peak concentrations of 1-10 µM in patient sera, but at these concentration(s) known nitroreductase (NTR) PCEs for this prodrug show low activity. Furthermore, recombinant PCE-expressing *Clostridium* strains that are efficacious, stable and disabled have not been reported. Here a novel nitroreductase, namely NmeNTR, is identified from *Neisseria meningitides*, which is able to activate CB1954 at clinically-achievable serum concentrations ($K_m^{CB1954}=2.47$ µM). An NmeNTR expression cassette, which does not contain an antibiotic resistance marker, was stably localised to the chromosome of *Clostridium sporogenes* using a new integration method, and the strain was disabled for safety and containment by making it a uracil auxotroph. The efficacy of a combination therapy using this system was demonstrated in a mouse xenograft model of human colon carcinoma. Substantial tumour suppression was achieved, and several animals were cured. These encouraging data suggest that the novel enzyme and strain engineering approach represent a promising platform for the clinical development of *Clostridium*-Directed Enzyme Prodrug Therapy (CDEPT).

Materials and Methods

Enzyme Screening

Genes encoding homologs of *E. coli* NfnB and *Bacillus amyloliquefaciens* YwrO from several bacteria were cloned into an *E. coli* expression vector for screening (see Methods below). These were the NfnB homolog from *Neisseria meningitidis* MC58 ('NmeNTR', accession number Q9K022), the NfnB homolog from *Haemophilus somnus* 129PT ('HsoNTR', accession number ZP_00122352.1), the NfnB homolog from *Burkholderia fungorum* LB400 ('BfuNTR', accession number ZP_00029570.1), the YwrO homolog from *Vibrio cholerae* ('VchYwrO', accession number Q9KNX3), the YwrO homolog from *Rhodobacter sphaeroides* ('RspYwrO', accession number ZP_00007082.1), and two YwrO homologs from *Pseudomo-* nas aeruginosa ('PaeYwrO1', accession number Q9HUJ0; and 'PaeYwrO2', accession number Q9I4B3).

In an initial screen for functional expression of each of the cloned genes, specific menadione reductase activity was determined in lysates of *E. coli* cells containing the NfnB or YwrO homolog expression plasmid. Enzymes from these families are expected to be NAD(P)H-dependent quinone reductases regardless of their nitroreductase activity against CB1954, and a photospectrometric menadione reductase assay is available (see Methods below), so this approach provides a convenient means to assess functional expression. The specific menadione reductase activity of lysates containing NmeNTR, HsoNTR, VchYwrO, PaeYwrO1 or PaeYwrO2 were significantly elevated above the control, and hence scored as functionally expressed; while RspYwrO and BfuNTR were not.

To screen for CB1954 nitroreductase activity of each of the functionally expressed genes, lysates of *E. coli* cells containing the NfnB or YwrO homolog expression plasmid were added to reaction mixtures containing CB1954 and the concentration of CB1954 was monitored by HPLC (see Methods below). Lysates containing NmeNTR or HsoNTR caused a decrease in CB1954 concentration, indicating nitroreductase activity against CB1954. Such activity was not observed in the lysates containing VchYwrO, PaeYwrO1 or PaeYwrO2.

Attempted Marker Removal Using FLP

In the first approach to construction of therapeutic strains, the NmeNTR and *E. coli* NfnB expression cassettes were inserted into the pyrF locus of the *C. sporogenes* chromosome using the pyrF-specific Group II intron plasmid pMTL007C-E2::Csp-pyrF-595s (1, 2) as described in Methods below. Insertions made in this way also contain the marker gene ermB, which confers resistance to the antibiotic erythromycin, an undesirable feature in a therapeutic strain. The ermB gene is flanked by flippase recognition target (FRT) sites, potentially allowing marker removal using FLP recombinase (3).

The FLP recombinase expression plasmid pMTL8515-PPS-flp3 (2) was introduced into the recombinant *C. sporogenes* strain containing the integrated NmeNTR expression cassette and ermB by conjugation from an *E. coli* donor. Three isolated transconjugant clones containing the FLP plasmid were each cultivated overnight at 30° C. in non-selective TYG (a complex growth medium), then single colonies were obtained by plating dilutions onto non-selective TYG plates. The overnight cultures were also sub-cultured by 1:100 dilution into fresh non-selective TYG, incubated overnight at 30° C., and single colonies were obtained by plating these second overnight cultures onto non-selective TYG plates. For each of the three isolated transconjugant clones, 16 single colonies from the first overnight culture and 34 single colonies from the second overnight culture were screened for FLP recombinase-mediated excision of the ermB marker by replica-plating colonies onto TYG plates supplemented with thiamphenicol and TYG plates supplemented with erythromycin. Resistance to thiamphenicol is encoded by the FLP plasmid, and resistance to erythromycin is encoded by the ermB gene. All clones grew on erythromycin, indicating that FLP recombinase-mediated excision of the ermB marker had not occurred in any clone.

Construction of Plasmids for Expression of Enzymes in *E. coli*

The genes encoding the candidate proteins VchYwrO, RspYwrO, NmeNTR, HsoNTR, BfuNTR, PaeYwrO1 and PaeYwrO2 were PCR-amplified from genomic DNA template or crude cell lysates using the forward and reverse primers of the same names with the suffix -F or -R respectively (Table S1). PCR products were cloned into pCR2.1 using TOPO TA Cloning Kit (Invitrogen) in accordance with the manufacturer's instructions. *E. coli* strain TOP10 (Invitrogen) was used as the host for all cloning and expression. The gene encoding HsoNTR contained an internal NdeI site, and this was silenced by overlap extension PCR in order that the NdeI site introduced by the forward primer HsoNTR-F would be unique, facilitating subsequent sub-cloning: One portion of the gene was PCR-amplified from pCR2.1::HsoNTR plasmid DNA template using the primers HsoNTR-F and HsoNTR-NdeI-A, and the remainder was PCR-amplified using the primers HsoNTR-NdeI-B and HsoNTR-R. The two PCR products were gel-purified and used as templates in an overlap extension PCR using the outer primers HsoNTR-F and HsoNTR-R. The resulting gene encodes an identical protein, but lacks the internal NdeI site.

The genes encoding NmeNTR and HsoNTR were later PCR-amplified from the relevant pCR2.1 derivatives using primers NmeNTR-F and NmeNTR-H6-R, or HsoNTR-F and HsoNTR-H6-R, respectively, yielding genes encoding proteins with carboxy-terminal six-histidine affinity tags.

Each gene was sub-cloned from pCR2.1 into the *E. coli* constitutive expression plasmid pMTL1015 (4) using restriction endonuclease sites NdeI and PstI, or NdeI and XbaI, which had been introduced into the PCR products by the primers. This placed expression of the genes under the control of the plasmid-borne promoter and RBS originating from the mdh gene of *E. coli*.

Enzyme Characterization

Lysates of *E. coli* clones containing pMTL1015-based enzyme expression plasmids were prepared for preliminary characterisation of enzyme activities. Clones were grown overnight in LB supplemented with 12.5 µg/ml tetracycline (to select for the plasmid) at 37° C. and 200 rpm shaking, and cells were harvested by centrifugation. Cell pellets were lysed either by sonication following re-suspension in 10 mM Tris HCl (pH 7.5) or using BugBuster protein extraction reagent (Novagen) in accordance with the manufacturer's instructions.

For determination of CB1954 nitroreductase kinetic parameters, six-histidine affinity-tagged enzymes were purified from cell lysates purified using a Novagen His-Bind kit in accordance with the manufacturer's instructions.

Menadione reductase activity was determined by the method of Knox (5). Cuvettes containing assay buffer (10 mM Tris HCl, pH 7.5) were pre-warmed to 37° C. To these 10 µM menadione, 1 mM NADH or NADPH, and 70 µM bovine cytochrome C were added. Reactions were started by the addition of enzyme (either crude lysate or purified enzyme) and prompt mixing. Reduction of cytochrome C was recorded by measuring increase in absorbance at 550 nm. Specific activities were calculated using the total protein concentrations of cell lysates, which were determined using the Bradford reagent (Sigma-Aldrich). Aliquots of cell lysates were mixed with 250 µl of Bradford reagent and incubated in the dark at room temperature for 5 min before absorbance was measured at 595 nm. Absorbance values were compared to those obtained using known concentrations of bovine serum albumin.

CB1954 nitroreductase activity was determined essentially as described by Anlezark (6). Reaction mixtures containing 500 µM NADH or NADPH and a small quantity of enzyme (either crude lysate or purified enzyme) were assembled in pre-warmed (to 37° C.) 100 mM sodium phosphate buffer (pH 7.0), and started with the addition of 100 μM CB1954 and prompt mixing.

To determine initial reaction rates during preliminary screening of CB1954 nitroreductase candidates, aliquots of the reaction mixtures taken at various times were injected into a Partisphere SCX (100×4.7 mm) HPLC column and eluted isocratically at 2 ml/min with 130 mM $NaH_2PO_4$ (pH 5.0). Eluates were continuously monitored at 260 nm and 325 nm, and the absorbance spectra of eluting components recorded using a photodiode array detector. Peaks were identified with reference to standards and/or by their known absorbance spectra (7) and anticipated column retention times as appropriate. Rates were determined based on the decrease in the area under the CB1954 peak over time, normalised to the known starting concentration of 100 μM using the peak from the zero timepoint sample.

To determine initial reaction rates and CB1954 nitroreduction products in later experiments with purified proteins, peaks were identified as before, and rates were determined based on the increase in the area under the 4-hydroxylamine derivative peak over time, normalised using enzymatically-synthesised 4-hydroxylamine standards.

Construction of Recombinant *C. sporogenes*

*C. sporogenes* was grown in static culture at 37° C. under an anaerobic atmosphere of $N_2:H_2:CO_2$ (80:10:10, vol:vol:vol) in an anaerobic workstation (Don Whitley, UK) using media pre-reduced overnight under the same conditions.

The NmeNTR and *E. coli* NfnB expression cassettes were initially inserted into the *C. sporogenes* chromosome using the ClosTron method as described previously (1, 2). This approach makes directed chromosomal insertions by employing a modified bacterial Group II intron, which is a type of mobile retro-element (8). The target site specificity of a particular Group II intron depends upon a small region of the intron RNA, and the corresponding intron-encoding DNA sequence can be rationally modified to re-target the intron (2, 9). An intron variant, Csp-pyrF-595s, was previously constructed (1) which targets pyrF, a gene involved in pyrimidine biosynthesis. This target site specificity was chosen for use in the present study, because cells in which pyrF is inactivated are uracil auxotrophs and effectively disabled from growth in the environment. The Csp-pyrF-595s intron region conferring target specificity was sub-cloned into pMTL007C-E2 (2) to construct pMTL007C-E2::Csp-pyrF-595s, a vector suitable for the Group II intron-mediated delivery of expression cassettes to the pyrF locus of *C. sporogenes*. Each expression cassette was inserted into the unique SalI site of pMTL007C-E2::Csp-pyrF-595s. Next, the plasmid was transferred into *C. sporogenes* by conjugation from a *E. coli* donor strain CA434, and transconjugant clones were selected on plates supplemented with thiamphenicol, resistance to which is encoded by the plasmid (2). The Group II intron, including the expression cassette and an ermB erythromycin resistance marker, is constitutively expressed and irreversibly inserted into a specific target site in a process termed retro-transposition. Cells containing a chromosomal insertion are selected by sub-culturing transconjugant clones onto plates supplemented with erythromycin.

Attempts to remove the ermB erythromycin resistance marker from the above strains using FLP recombinase (see above, Attempted marker removal using FLP) were not successful, so the need for marker removal was circumvented by using a different integration approach. The NmeNTR and *E. coli* NfnB expression cassettes were each inserted into the integration vector pMTL-JH27, and in turn integrated into the pyrE locus using the procedure described previously (10). Plasmids were transferred into *C. sporogenes* by conjugation from the *E. coli* donor strain CA434, and transconjugant clones were selected on plates supplemented with thiamphenicol, resistance to which is encoded by the plasmid. First, single-crossover clones were enriched by sub-culturing on thiamphenicol plates, then stable double-crossover clones were isolated by transferring cells onto plates supplemented with 5-fluoroorotic acid (10). Loss of the plasmid (which encodes thiamphenicol resistance) was confirmed by replica-plating colonies onto unsupplemented TYG plates and TYG plates supplemented with thiamphenicol.

Characterization of Recombinant *C. sporogenes*

Successful integration of the NmeNTR and *E. coli* NfnB expression cassettes in *C. sporogenes* strains N1 and E1, respectively, was verified by PCR (FIG. 2 B). Strains N1, E1 and the wild-type were grown overnight in TYG broth, cells were harvested by centrifugation, and genomic DNA was extracted using the Qiagen DNeasy Blood & Tissue Kit in accordance with the manufacturer's instructions, including the recommended modifications for gram-positive bacteria. PCR was performed using Phusion polymerase (NEB) and chromosome-specific primer Csp-pyrD-sF2 in combination with insert-specific primer M13F (for primer sequences, see Table S1).

*C. sporogenes* strains were tested for uracil auxotrophy/prototrophy by picking fresh colonies grown on TYG plates and sub-culturing them onto plates of *Clostridium botulinum* defined minimal medium MI (11) supplemented with 0 or 40 μg/ml uracil, then incubating plates at 37° C. for 24 h. The wild-type grew equally well with or without the uracil supplement, whereas the uracil auxotroph strains grew similarly to the wild-type on the uracil-supplemented plates, but showed no growth on the unsupplemented plates.

Specific menadione reductase activities of lysates of *C. sporogenes* were determined as described for *E. coli* above, except lysates were prepared from cultures in the late exponential phase of growth, rather than from overnight cultures, to avoid issues associated with sporulation and heterogeneity in overnight cultures of *C. sporogenes*. Cells were lysed using BugBuster Protein Extraction Reagent (Novagen) in accordance with the manufacturer's instructions, including rLysozyme and Benzonaze nuclease.

To evaluate the ability of strains to form spores, TYG broth was inoculated to an $OD_{600}$ of 0.05 using a starter culture grown overnight in the same medium. After incubation at 37° C. for five days, the titre of heat-resistant colony-forming units (a measure of spore titre) was determined by heat-treating samples of cultures at 80° C. for 20 minutes to inactivate vegetative cells, then serially-diluting and plating the samples onto TYG agar plates.

Mouse Xenograft Tumour Model

Human colorectal HCT116 carcinoma cells were grown in DMEM medium supplemented with 10% FBS, trypsinized and injected subcutaneously in 100 μl PBS/ . . . % matrigel at a concentration of $5.10^6$ cells in the abdominal flank of adult NMRI nu/nu mice. As soon as tumours were palpable, tumour volumes were determined three times per week by measuring three orthogonal diameters using calipers. Volumes were calculated according to the formula V=A×B×C×/6. All experiments were conducted in accordance with local institutional guidelines of the University of Leuven, approved by the animal ethics committee and procedures were according to the guidelines defined by the UKCCCR (12). Treatment was initiated when tumours reached a volume of ~250 $mm^3$. Five days post spore injection ($5.10^7$ cfu/100 μl), sham or prodrug treatment was started. CB1954 was prepared as described previously (13) and administered intraperitoneally (i.p.) at a concentration of 15 mg/kg for five consecutive days. At the end of the follow-up period, tumours and normal tissues were excised, ground and serially diluted to determine colonization levels (14). Tumour growth delay was determined for each individual tumour within the different groups as the time necessary to reach three times their initial volume at the start of the treatment. One-way ANOVA with a Tukey's posttest was used to determine statistical significance between the different growth curves.

Results

A Novel NTR which Efficiently Activates CB1954 at Clinically-achievable Concentrations Known enzymes with NTR activity against CB1954 are NAD(P)H-dependent quinone reductases belonging to one of two large protein families, Pfam PF00881 'Nitroreductase' and Pfam PF02525 'Flavodoxin_2', such as *E. coli* NfnB (20) and *Bacillus amyloliquefaciens* YwrO (21) respectively. homologs of these proteins were identified in the genome sequences of other organisms, and their activity against CB1954 was investigated. Each gene encoding a candidate CB1954-activating enzyme was cloned in an *E. coli* expression vector, and crude cell lysates were used in initial screens for functional expression, and then to test for CB1954 nitroreductase activity using an HPLC assay. CB1954 was rapidly consumed by cell lysates containing the NfnB homolog from *Haemophilus somnus* 129PT or *Neisseria meningitidis* MC58. Therefore these two enzymes, designated HsoNTR and NmeNTR respectively, were studied in more detail.

NmeNTR and HsoNTR were each affinity-tagged, overexpressed, purified, and the CB1954 nitroreductase activities of the purified proteins characterized using the HPLC assay. The reaction products and kinetic parameters of these enzymes with respect to CB1954 and NADH were determined (Table 1). Both NmeNTR and HsoNTR reduce CB1954 only at the 4-nitro group, producing the highly toxic 4HX derivative. This contrasts with the widely-studied *E. coli* NfnB which reduces CB1954 at either the 4-nitro group or 2-nitro group, producing equimolar quantities of the 4HX derivative and much less toxic 2-hydroxylamine (2HX) derivative (5-(aziridin-1-yl)-2-hydroxylamino-4-nitrobenzamide) (22, 23). Moreover, the kinetic parameters of HsoNTR and NmeNTR differ dramatically from those of *E. coli* NfnB and other published enzymes (Table 1). Crucially, NmeNTR is the first reported enzyme with a $K_m^{CB1954}$ lower than 6.3 µM, the maximum concentration of CB1954 which can be safely achieved in patient serum. NmeNTR would therefore approach saturation with CB1954 in a therapeutic regime using the maximum clinically-recommended dose, so the prodrug would be efficiently activated and high levels of tumour-specific cytotoxicity achieved.

Construction of NTR-expressing *Clostridium* Strains that are Stable, Disabled, and Lack Antibiotic Marker Genes To establish whether the apparently superior kinetic properties of NmeNTR would result in improved therapeutic performance, strains of *Clostridium sporogenes* NCIMB 10696 expressing NmeNTR or *E. coli* NfnB were constructed and compared in an in vivo model. *C. sporogenes* NCIMB 10696 is one of the tumour-targeting *Clostridium* strains currently most studied as a potential therapeutic agent (13-17) along with *Clostridium novyi* NT (24-27). An expression cassette was constructed using the strong, constitutive promoter from the ferredoxin gene fdx of *C. sporogenes* to direct expression of NmeNTR from a synthetic coding sequence sequence with codon usage optimised to suit *C. sporogenes*. An equivalent expression cassette for *E. coli* NfnB was also constructed for comparison.

In previous CDEPT studies nitroreductases have been expressed using autonomous plasmids, but these exhibit segregational instability (28), causing the proportion of plasmid-containing cells in a population to decrease during growth. It follows that expression of a plasmid-borne NTR is expected to be poor and heterogenous in a tumour colonized through many generations of bacterial growth (29) following the initial infiltration of a small number of spores. Plasmids also carry a risk of transfer to other organisms. To overcome these issues, the expression construct was localized to the chromosome, which has complete segregational stability and no mechanism for transfer. The insertion of heterologous expression constructs into the chromosome of tumour-targeting *Clostridium* sp. has not previously been reported, but suitable methods for chromosomal integration in *C. sporogenes* have recently been developed (30-32).

The NmeNTR and *E. coli* NfnB expression cassettes were initially inserted into the *C. sporogenes* chromosome using the ClosTron method (30, 31) which employs a modified bacterial Group II intron (a type of mobile retro-element (33)) to deliver the sequence of interest. Recombinant clones were isolated using the antibiotic erythromycin, resistance to which is conferred by the marker gene ermB within the insertion. As antibiotic resistance is undesirable in therapeutic strains, subsequent removal of ermB from the chromosome using FLP recombinase was attempted, but was unsuccessful.

To circumvent the need for marker removal, recently-developed integration method, "ACE", was used in which an antibiotic selection marker need not be incorporated into the chromosome along with the expression cassette (32). The NmeNTR and *E. coli* NfnB expression cassettes were inserted into the *C. sporogenes* chromosome using integration vector pMTL-JH27, which targets pyrE, a gene involved in pyrimidine biosynthesis. By inactivating pyrE during integration, recombinant cells are also uracil auxotrophs and effectively disabled from growth in the environment. Using this approach, the desired recombinant *C. sporogenes* strains containing *E. coli* NfnB and NmeNTR were readily obtained, and were designated E1 and N1, respectively (FIGS. 2A and B). The 'empty' vector pMTL-JH27 was previously used to generate a pyrE mutant without an expression cassette (32) which was used as a control in this study (FIG. 2A).

Strain Characterisation In Vitro

To determine whether the heterologous nitroreductases were functionally expressed by strains E1 and N1, the menadione reductase activity in cell lysates of these strains was measured and compared to the wild-type and the pyrE mutant. Cells lysates of both E1 and N1 contained menadione reductase activity elevated significantly above the endogenous levels measured in the controls (FIG. 2C).

The disablement of E1, N1 and the pyrE mutant was confirmed by sub-culturing cells of these strains and the wild-type from the complex medium TYG onto plates of a defined growth medium either with or without supplementary uracil. The wild-type grew equally well with or without the uracil supplement, whereas E1, N1 and the pyrE mutant were unable to grow without exogenous uracil, confirming their disablement, a uracil auxotrophic phenotype.

CDEPT depends upon the ability of *Clostridium* to form spores, the metabolically-dormant, highly-robust form suitable for intravenous administration and for long periods of storage. Therefore it was necessary to determine whether the ability of the recombinant strains to form spores had been affected by the inactivation of pyrE, the addition of the NTR expression cassettes, or the sub-culturing steps during the genetic modification procedure. The wild-type, E1, N1 and the pyrE mutant were cultivated in TYG broth, in which the wild-type forms spores over time. A spo0A mutant, which is completely unable to form spores, was also included as a control (30). Samples taken over several days were heated to inactivate vegetative cells, and the titre of heat-resistant colony-forming units (corresponding to viable spores) was determined by dilution plating (FIG. 2D). The spo0A mutant formed no colonies following heat treatment, confirming that the procedure inactivated all vegetative cells. E1, N1 and the pyrE mutant were all able to form spores, and did so at the same rate as the wild-type, and to the same final titre.

CDEPT Treatment of Tumours In Vivo

Since strains E1 and N1 express stably-integrated NTR under the regulatory control of a strong promoter without inclusion of any antibiotic resistance gene, it was next determined whether administration of these clinically-applicable strains in combination with prodrug administration to tumour-bearing animals would result in anti-tumour efficacy. It was first evaluated whether inactivation of pyrE affected the tumour-colonizing capacity of systemically administered spores. Mice bearing subcutaneously transplanted HCT116 tumours were injected and tumour colonization tested seven days later. Wild-type and ΔpyrE $C.$ $sporogenes$ colonized the tumour equally well. On average $10^9$ cfu were found per gram of tumour tissue. Colonization was also confirmed by gram staining. In tumours, $C.$ $sporogenes$ vegetative cells are visible as purple, gram-positive rods (FIG. 3 C). As expected, $C.$ $sporogenes$ vegetative cells could not be detected in any of the normal tissues investigated. Disablement of the strain by knocking out pyrE thus did not affect the excellent tumour colonizing capacity of $C.$ $sporogenes$. To investigate the in vivo anti-tumour efficacy, the effect was compared in animals that received (1) no treatment, (2) prodrug alone, (3) pyrE mutant spores alone, (4) pyrE mutant spores in combination with CB1954 and (4) N1 or E1 spores in combination with CB1954; each in a standard experimental tumour growth delay setting. This choice of groups allowed comparison of the contribution of the two major improvements reported here, stable integration and improved enzyme kinetics. Spores were collected, quantified and intravenously administered at a concentration of $5.10 \times 10^7$ per animal when tumours reached a volume of ~250 mm$^3$, followed five days later by sham or prodrug administration. By randomly analyzing tumours across the different groups at day five, colonization of the tumours was confirmed at the start of prodrug administration. In line with previous observations (16) administration of prodrug alone did not result in any effect, whereas a small growth delay could be observed upon administration of spores alone or in combination with CB1954 (FIG. 3 A). Strikingly, combining E1 or N1 with CB1954 resulted in a significant growth delay, the effect being most pronounced for N1 ($p<0.001$, one way ANOVA, FIG. 3 B). This indicates that the improved enzyme kinetics that allow conversion of the prodrug to its toxic metabolite at a much lower concentration as compared to E1, highly contribute to the observed effect. The most striking effect observed was the disappearance of several tumours in both CDEPT groups. In the E1/CB1954 group, two out of 16 tumours completely disappeared and in the N1/CB1954 four out of 16 tumours completely disappeared. During the treatment, a mild and transient weight loss could be observed and the animals recovered completely during further follow-up time. To prove the stability of the NTR integration in the $C.$ $sporogenes$ chromosome, PCR analysis was performed on lysates of tumours, using strain-specific primers. In all cases, strain specific signals could be detected thereby confirming stability of the integrated construct.

Discussion

The poor activity of known nitroreductases at clinically-relevant CB1954 concentrations has led to several previous attempts to obtain an enzyme with more suitable kinetic properties, by screening native enzymes (21, 35-38) and/or protein engineering (38-42). However, NmeNTR, the $N.$ $meningitidis$ homolog of $E.$ $coli$ nitroreductase NfnB reported here, is the first example of an enzyme with a $K_m^{CB1954}$ value that can be exceeded by the clinically-achievable serum concentration of the prodrug. This $K_m^{CB1954}$ value (2.47 µM) is seven-fold lower than the lowest previously reported (NfsA, 18 µM, Table 1). This key improvement makes NmeNTR much more suitable for clinical application than other known enzymes.

NmeNTR reduces only the 4-nitro group of CB1954, producing the highly-cytotoxic 4HX derivitative, unlike $E.$ $coli$ NfnB which produces both the 4HX and 2HX derivitatives in similar proportions (22, 23). Among the enzymes whose CB1954 nitroreductase activity has now been characterised, specificity for the 4-nitro group appears to be typical (Table 1). $E.$ $coli$ NfnB, although the most widely studied CB1954 nitroreductase, is unusual in this respect. The 4HX derivitative is far more cytotoxic than the 2HX derivitative (43) which suggests that an enzyme such as NmeNTR with specificity for the 4-nitro group would lead to greater tumour-specific cytotoxicity.

By localising expression cassettes to the chromosome using double crossover homologous recombination, stable strains have been constructed that lack both antibiotic resistance markers and any mechanism for transfer of the heterologous sequence. This feature represents a major improvement over previous studies in terms of efficacy and safety, as the instability of known plasmid replicons in $C.$ $sporogenes$ has been established (28) and transfer of natural and recombinant conjugal plasmids and transposons is known to occur in $C.$ $sporogenes$ and close relatives.

$C.$ $sporogenes$ is naturally confined to the hypoxic tumour core by oxygen, and the disabling pyrE mutation would serve to severely limit growth of modified strains in the environment in the event of accidental release from a clinical setting. Tumour containment and/or targeting features have been described for other recombinant bacterial strains with anti-tumour potential, such as $Salmonella$ (10, 11). The use of elegant synthetic regulatory mechanisms has also been proposed for containment (4) but physiological mechanisms may be more appropriate. Any system in which containment depends upon the continued function of introduced component(s) will be vulnerable to failure through spontaneous loss-of-function mutations. Such mutations are inevitable at some frequency, and mutants would have a selective advantage for growth outside the tumour, so these systems would be inherently fragile. In contrast, no loss-of-function mutation is likely to allow an auxotrophic mutant of a strict $anaerobe$, as reported here, to escape the tumour environment.

The approach to constructing stable, disabled, antibiotic marker-free strains of $Clostridium$ expressing heterologous genes represents a platform for future efforts to build upon, as it provides a tumour-specific delivery system for the development of safe and effective gene therapies. The novel PCE NmeNTR in combination with CB1954 is a promising candidate.

REFERENCES

1. NIH (2002) Assessment of adenoviral vector safety and toxicity: report of the National Institutes of Health Recombinant DNA Advisory Committee. *Hum Gene Ther* 13:3-13.
2. Hacein-Bey-Abina S et al. (2008) Insertional oncogenesis in 4 patients after retrovirus-mediated gene therapy of SCID-X1. *J Clin Invest* 118:3132-3142.
3. Breitbach C J et al. (2011) Intravenous delivery of a multi-mechanistic cancer-targeted oncolytic poxvirus in humans. *Nature* 477:99-102.
4. Forbes N S (2010) Engineering the perfect (bacterial) cancer therapy. *Nat Rev Cancer* 10:785-794.
5. Malmgren R A, Flanigan C C (1955) Localization of the vegetative form of *Clostridium tetani* in mouse tumours following intravenous spore administration. *Cancer Res* 15:473-478.
6. Moese J R, Moese G (1964) Oncolysis by clostridia. I. Activity of *Clostridium butyricum* (M-55) and other non-pathogenic clostridia against the Ehrlich carcinoma. *Cancer Res* 24:212-216.
7. Carey R W, Holland J F, Whang H Y, Neter E, Bryant B (1967) Clostridial oncolysis in man. *Eur J Cancer* 3:37-46.
8. Pipiya T et al. (2005) Hypoxia reduces adenoviral replication in cancer cells by downregulation of viral protein expression. *Gene Ther* 12:911-917.
9. Shen B H, Hermiston T W (2005) Effect of hypoxia on Ad5 infection, transgene expression and replication. *Gene Ther* 12:902-910.
10. Zhao M et al. (2005) Tumour-targeting bacterial therapy with amino acid auxotrophs of GFP-expressing *Salmonella typhimurium*. *Proc Natl Acad Sci USA* 102:755-760.
11. Zhao M et al. (2007) Monotherapy with a tumour-targeting mutant of *Salmonella typhimurium* cures orthotopic metastatic mouse models of human prostate cancer. *Proc Natl Acad Sci USA* 104:10170-10174.
12. Minton N P, Brown J M, Lambin P, Anné J (2005) *Clostridia—Biotechnology and Medical Applications*. eds Bahl H, Dürre P (Wiley-VCH Verlag GmbH).
13. Lemmon M J et al. (1997) Anaerobic bacteria as a gene delivery system that is controlled by the tumour microenvironment. *Gene Ther* 4:791-796.
14. Fox M E, Lemmon M J, Giaccia A J, Minton N P, Brown J M (2000) Genetically modified *Clostridium* for gene therapy of tumours. *Methods Mol Med* 35:413-418.
15. Liu S C, Minton N P, Giaccia A J, Brown J M (2002) Anticancer efficacy of systemically delivered anaerobic bacteria as gene therapy vectors targeting tumour hypoxia/necrosis. *Gene Ther* 9:291-296.
16. Theys J et al. (2006) Repeated cycles of *Clostridium*-directed enzyme prodrug therapy result in sustained anti-tumour effects in vivo. *Br J Cancer* 95:1212-1219.
17. Liu S-C et al. (2008) Optimized *Clostridium*-directed enzyme prodrug therapy improves the antitumour activity of the novel DNA cross-linking agent PR-104. *Cancer Res* 68:7995-8003.
18. Chung-Faye G et al. (2001) Virus-directed, enzyme prodrug therapy with nitroimidazole reductase: a phase I and pharmacokinetic study of its prodrug, CB1954. *Clin Cancer Res* 7:2662-2668.
19. Palmer D H, Milner A E, Kerr D J, Young L S (2003) Mechanism of cell death induced by the novel enzyme-prodrug combination, nitroreductase/CB1954, and identification of synergism with 5-fluorouracil. *Br J Cancer* 89:944-950.
20. Michael N P, Brehm J K, Anlezark G M, Minton N P (1994) Physical characterisation of the *Escherichia coli* B gene encoding nitroreductase and its over-expression in *Escherichia coli* K12. *FEMS Microbiol Lett* 124:195-202.
21. Anlezark G M et al. (2002) *Bacillus amyloliquefaciens* orthologue of *Bacillus subtilis* ywrO encodes a nitroreductase enzyme which activates the prodrug CB 1954. *Microbiology* 148:297-306.
22. Anlezark G M et al. (1992) The bioactivation of 5-(aziridin-1-yl)-2,4-dinitrobenzamide (CB1954)-I. Purification and properties of a nitroreductase enzyme from *Escherichia coli*—a potential enzyme for antibody-directed enzyme prodrug therapy (ADEPT). *Biochem Pharmacol* 44:2289-2295.
23. Knox R J, Friedlos F, Sherwood R F, Melton R G, Anlezark G M (1992) The bioactivation of 5-(aziridin-1-yl)-2,4-dinitrobenzamide (CB1954)-II. A comparison of an *Escherichia coli* nitroreductase and Walker D T diaphorase. *Biochem Pharmacol* 44:2297-2301.
24. Bettegowda C et al. (2006) The genome and transcriptomes of the anti-tumour agent *Clostridium novyi*-NT. *Nat Biotechnol* 24:1573-1580.
25. Diaz L A et al. (2005) Pharmacologic and toxicologic evaluation of *C. novyi*-NT spores. *Toxicol Sci* 88:562-575.
26. Smith A B et al. (2005) Discodermolide analogues as the chemical component of combination bacteriolytic therapy. *Bioorg Med Chem Lett* 15:3623-3626.
27. Dang L H, Bettegowda C, Huso D L, Kinzler K W, Vogelstein B (2001) Combination bacteriolytic therapy for the treatment of experimental tumours. *Proc Natl Acad Sci USA* 98:15155-15160.
28. Heap J T, Pennington O J, Cartman S T, Minton N P (2009) A modular system for *Clostridium* shuttle plasmids. *J Microbiol Methods* 78:79-85.
29. Danino T, Lo J, Prindle A, Hasty J, Bhatia S N (2012) In Vivo Gene Expression Dynamics of Tumour-Targeted Bacteria. *ACS Synthetic Biology* 1:465-470.
30. Heap J T, Pennington O J, Cartman S T, Carter G P, Minton N P (2007) The ClosTron: a universal gene knock-out system for the genus *Clostridium*. *J Microbiol Methods* 70:452-464.
31. Heap J T et al. (2010) The ClosTron: Mutagenesis in *Clostridium* refined and streamlined. *J Microbiol Methods* 80:49-55.
32. Heap J T et al. (2012) Integration of DNA into bacterial chromosomes from plasmids without a counter-selection marker. *Nucleic Acids Res* 40:59.
33. Lambowitz A M, Zimmerly S (2004) Mobile group II introns. *Annu Rev Genet* 38:1-35.
34. Berg P, Baltimore D, Brenner S, Roblin R O, Singer M F (1975) Summary statement of the Asilomar conference on recombinant DNA molecules. *Proc Natl Acad Sci USA* 72:1981-1984.
35. Emptage C D, Knox R J, Danson M J, Hough D W (2009) Nitroreductase from *Bacillus licheniformis*: a stable enzyme for prodrug activation. *Biochem Pharmacol* 77:21-29.
36. Vass S O, Jarrom D, Wilson W R, Hyde E I, Searle P F (2009) *E. coli* NfsA: an alternative nitroreductase for prodrug activation gene therapy in combination with CB1954. *Br J Cancer* 100:1903-1911.
37. Prosser G A et al. (2010) Discovery and evaluation of *Escherichia coli* nitroreductases that activate the anticancer prodrug CB1954. *Biochem Pharmacol* 79:678-687.

38. Swe P M et al. (2012) Targeted mutagenesis of the *Vibrio fischeri* flavin reductase FRase I to improve activation of the anticancer prodrug CB1954. *Biochem Pharmacol* 84:775-783.
39. Grove J I et al. (2003) Generation of *Escherichia coli* nitroreductase mutants conferring improved cell sensitization to the prodrug CB1954. *Cancer Res* 63:5532-5537.
40. Race P R et al. (2007) Kinetic and structural characterisation of *Escherichia coli* nitroreductase mutants showing improved efficacy for the prodrug substrate CB1954. *J Mol Biol* 368:481-492.
41. Jarrom D et al. (2009) Steady-state and stopped-flow kinetic studies of three *Escherichia coli* NfsB mutants with enhanced activity for the prodrug CB1954. *Biochemistry* 48:7665-7672.
42. Jaberipour M et al. (2010) Testing double mutants of the enzyme nitroreductase for enhanced cell sensitisation to prodrugs: effects of combining beneficial single mutations. *Biochem Pharmacol* 79:102-111.
43. Knox R J, Friedlos F, Jarman M, Roberts J J (1988) A new cytotoxic, DNA interstrand crosslinking agent, 5-(aziridin-1-yl)-4-hydroxylamino-2-nitrobenzamide, is formed from 5-(aziridin-1-yl)-2,4-dinitrobenzamide (CB 1954) by a nitroreductase enzyme in Walker carcinoma cells. *Biochem Pharmacol* 37:4661-4669.
44. Helsby N A, Ferry D M, Patterson A V, Pullen S M, Wilson W R (2004) 2-Amino metabolites are key mediators of CB 1954 and SN 23862 bystander effects in nitroreductase GDEPT. *Br J Cancer* 90:1084-1092.
45. Lambin P et al. (1998) Colonisation of *Clostridium* in the body is restricted to hypoxic and necrotic areas of tumours. *Anaerobe* 4:183-188.

TABLE 1

CB1954 nitroreductase properties of selected enzymes.

| Enzyme | $K_{cat}$ (S$^{-1}$) | $K_m^{CB1954}$ (μM) | $K_{cat}/K_m^{CB1954}$ (s$^{-1}$μM$^{-1}$) | $K_m^{NADH}$ (μM) | Products | Source/Comment |
|---|---|---|---|---|---|---|
| NmeNTR | 4.04 (NADH) 15.23 (NADPH) | 2.47 | 1.636 (NADH) 6.166 (NADPH) | 188 | 4HX | NTR from *Neisseria meningitidis* MC58 (this study). Lowest $K_m^{CB1954}$ and highest $K_{cat}/K_m^{CB1954}$ values of any reported enzyme. |
| HsoNTR | 3.5 (NADH) 13.13 (NADPH) | 22.03 | 0.159 (NADH) 0.596 (NADPH) | 644 | 4HX | NTR from *Haemophilus somnus* 129PT (this study). |
| NfnB | 6 | 862 | 0.007 | 6 | 4HX + 2HX | Widely-studied *E. coli* NTR (Knox et al., 1992). |
| NfnB N71S/F124K | 7.5 | 170 | 0.044 | 5 | 4HX + 2HX | Mutant obtained by protein engineering (Searle et al., 2004 and Race et al., 2007). |
| HinNTR | 56.2 | 690 | 0.081 | ND | 4HX | NTR from *Haemophilus influenzae* (Theys et al., 2006). Highest $K_{cat}$ value of any reported enzyme. |
| NfsA | 2.60 (NADH) 20.9 (NADPH) | 18 (NADH) 140 (NADPH) | 0.15 | ND | 2HX | A second *E. coli* NTR (Vass et al., 2009). |
| BliNTR | 6.4 | 30 | 0.213 | 820 | 4HX | NTR from *Bacillus licheniformis* (Emptage et al., 2009.) |
| Frase I F124W | 26.6 | 259 | 0.103 | ND | 4HX | Mutant of FRase 1 from *Vibrio fischeri* obtained by protein engineering (Swe et al., 2012). |

The enzymes shown include those with the most favourable values reported for $K_{cat}$, $K_m^{CB1954}$, and $K_{cat}/K_m^{CB1954}$.

The invention claimed is:

1. A method of treating a solid tumor cancer in a subject comprising the administration to the subject of an obligate anaerobic microorganism expressing a polypeptide having nitroreductase activity and/or the spores thereof, wherein the obligate anaerobic microorganism and/or spores thereof colonize a tumour of the subject, and wherein the polypeptide:
   exhibits preferential reduction of CB1954 to a 4-hydroxylamine (4HX) derivative instead of a 2-hydroxylamine derivative; and
   is capable of reducing CB1954 to the 4HX derivative with a $K_m$ of less than 30 micromolar; and
   wherein the polypeptide comprises or consists of the amino acid sequence of:
   a. SEQ ID NO: 1 (NmeNTR); or
   b. SEQ ID NO: 2 (HsoNTR).

2. The method of claim 1, further comprising the administration of a prodrug containing a nitro functional group to the subject.

3. The method according to claim 1 further comprising the administration of a prodrug comprising or consisting of CB1954 (5-(aziridin-1-yl)-2,4-dinitrobenzamide) or its analogue SN 23862 5-(N, N-bis(2-chloroethyl)amino)-2,4-dinitrobenzamide).

4. The method according to claim 1, wherein the obligate anaerobic microorganisms and/or spores are administered to the subject by intravenous administration.

5. The method according to claim 1, wherein the subject is colonised with the obligate anaerobic microorganism prior to administration of a prodrug containing a nitro functional group.

6. The method according to claim 1, wherein the obligate anaerobic microorganism is capable of sporulation.

7. The method according to claim 1, wherein the obligate anaerobic microorganism is administered in spore form.

8. The method according to claim 1, wherein at least about $5 \times 10^7$ spores of the obligate anaerobic microorganism are administered to the subject.

9. The method according to claim 1 further comprising administering a prodrug containing a nitro functional group at a dose of at least 15 mg/kg.

10. The method according to claim 1, wherein the polypeptide is capable of reducing CB1954 to the 4HX derivative with a $K_m$ of 25 micromolar or less.

11. The method according to claim 1, wherein the polypeptide is capable of reducing CB1954 to a 4-hydroxylamine (4HX) derivative substantially without producing the 2-hydroxylamine derivative.

12. The method according to claim 1, wherein the obligate anaerobic microorganism is a bacterium.

13. The method according to claim 1, wherein the obligate anaerobic microorganism is a bacterium of the class Clostridia.

14. The method according to claim 1, wherein the obligate anaerobic microorganism is a Clostridial species selected from the group consisting of:
c. *Clostridium sporogenes*; and
d. *Clostridium novyi*.

15. The method according to claim 1, wherein the obligate anaerobic microorganism is auxotrophic for one or more essential nutrient.

16. The method according to claim 1, wherein the obligate anaerobic microorganism does not comprise an exogenous antibiotic resistance gene.

17. The method according to claim 1, wherein the polypeptide is encoded on the chromosome of the obligate anaerobic microorganism.

18. A method of converting a prodrug to a drug active in situ in a tumour, such as a solid tumour in a subject in need thereof, comprising administering an obligate anaerobic microorganism and/or the spores thereof to the subject, wherein the obligate anaerobic microorganism and/or spores thereof expresses a polypeptide having nitroreductase activity, wherein the polypeptide:
  exhibits preferential reduction of CB1954 to a 4-hydroxylamine (4HX) derivative instead of a 2-hydroxylamine derivative; and
  is capable of reducing CB1954 to the 4HX derivative with a $K_m$ of less than 30 micromolar; and
wherein the polypeptide comprises or consists of the amino acid sequence of:
  a. SEQ ID NO: 1 (NmeNTR); or
  b. SEQ ID NO: 2 (HsoNTR).

* * * * *